(12) United States Patent
Donaldson et al.

(10) Patent No.: US 11,832,833 B2
(45) Date of Patent: Dec. 5, 2023

(54) PERCUTANEOUS ACCESS PATHWAY SYSTEM

(71) Applicant: Critical Innovations LLC, Inglewood, CA (US)

(72) Inventors: Ross I. Donaldson, Inglewood, CA (US); Oliver Buchanan, Inglewood, CA (US); Muhammed Hamdan, Inglewood, CA (US); Tim Fisher, Inglewood, CA (US); John Cambridge, Inglewood, CA (US); Jonathan Armstrong, Inglewood, CA (US)

(73) Assignee: Critical Innovations, LLC, Lawndale, CA (US)

( * ) Notice: Subject to any disclaimer, the term of this patent is extended or adjusted under 35 U.S.C. 154(b) by 302 days.

(21) Appl. No.: 16/948,885

(22) Filed: Oct. 5, 2020

(65) Prior Publication Data

US 2021/0106344 A1    Apr. 15, 2021

Related U.S. Application Data

(60) Provisional application No. 62/913,883, filed on Oct. 11, 2019.

(51) Int. Cl.
*A61B 17/16* (2006.01)
*A61B 17/00* (2006.01)
*A61B 17/34* (2006.01)

(52) U.S. Cl.
CPC .... *A61B 17/1695* (2013.01); *A61B 17/00234* (2013.01); *A61B 17/1615* (2013.01); *A61B 17/3423* (2013.01); *A61B 2017/00238* (2013.01); *A61B 2017/3425* (2013.01)

(58) Field of Classification Search
CPC .......... A61B 17/1695; A61B 17/00234; A61B 17/1615; A61B 17/3423; A61B 17/1637; A61B 17/1626; A61B 2017/00238; A61B 2017/3425; A61B 90/40; A61B 2090/034; A61B 2090/08021; A61B 2090/0813
See application file for complete search history.

(56) References Cited

U.S. PATENT DOCUMENTS

| | | | |
|---|---|---|---|
| 4,456,010 A * | 6/1984 | Reimels | B23B 51/10 408/139 |
| 5,207,681 A | 5/1993 | Ghadjar et al. | |
| 5,876,405 A | 3/1999 | Del et al. | |
| 5,891,100 A | 4/1999 | Fleckenstein | |
| 6,923,799 B1 | 8/2005 | Asfora | |

(Continued)

FOREIGN PATENT DOCUMENTS

| | | |
|---|---|---|
| DE | 102007060493 A1 | 6/2009 |
| EP | 3804638 A2 | 4/2021 |
| WO | 2015150844 A1 | 10/2015 |

OTHER PUBLICATIONS

European Search Report for Application No. 20200993.2, dated Apr. 30, 2021, 9 pages.

*Primary Examiner* — Shaun L David
*Assistant Examiner* — Rachael L Geiger
(74) *Attorney, Agent, or Firm* — Merchant & Gould P.C.

(57) ABSTRACT

An improved method and device are provided for forming and/or maintaining a percutaneous access pathway. The device generally comprises an access pathway. The provided assembly substantially reduces the possibility of injury while accessing and/or re-accessing a body space.

8 Claims, 20 Drawing Sheets

(56) References Cited

U.S. PATENT DOCUMENTS

| | | |
|---|---|---|
| 7,553,290 B1 | 6/2009 | Asfora |
| 7,694,821 B1 | 4/2010 | Asfora |
| 8,403,878 B2 | 3/2013 | Branch et al. |
| 8,679,088 B2 | 3/2014 | Abrahams |
| 9,155,555 B2 | 10/2015 | Obrien |
| 9,161,820 B2 | 10/2015 | Mark et al. |
| 9,211,163 B1 | 12/2015 | Jaramaz et al. |
| 9,616,203 B2 | 4/2017 | Donaldson |
| 10,046,147 B2 | 8/2018 | Donaldson |
| 10,314,952 B2 | 6/2019 | Donaldson |
| 10,814,119 B2 | 10/2020 | Donaldson et al. |
| 10,864,356 B2 | 12/2020 | Donaldson |
| 11,364,326 B2 | 6/2022 | Donaldson |
| 11,406,809 B2 | 8/2022 | Donaldson et al. |
| 2004/0034382 A1 | 2/2004 | Thomas |
| 2007/0270771 A1 | 11/2007 | Ralph et al. |
| 2008/0281343 A1 | 11/2008 | Dewey et al. |
| 2010/0034605 A1 | 2/2010 | Huckins et al. |
| 2013/0245629 A1 | 9/2013 | Xie |
| 2014/0046303 A1 | 2/2014 | Donaldson |
| 2015/0182733 A1 | 7/2015 | Donaldson |
| 2016/0000448 A1* | 1/2016 | Houussiere .......... A61B 17/1615 606/130 |
| 2017/0182229 A1 | 6/2017 | Donaldson |
| 2017/0197017 A1 | 7/2017 | Martin |
| 2018/0296808 A1 | 10/2018 | Donaldson |
| 2019/0091459 A1 | 3/2019 | Donaldson et al. |
| 2019/0117254 A1 | 4/2019 | Mark et al. |
| 2019/0255228 A1 | 8/2019 | Donaldson |
| 2021/0040883 A1 | 2/2021 | Donaldson et al. |
| 2021/0093843 A1 | 4/2021 | Donaldson |
| 2022/0323654 A1 | 10/2022 | Donaldson |
| 2022/0370780 A1 | 11/2022 | Donaldson et al. |

* cited by examiner

PERCUTANEOUS ACCESS PATHWAY SYSTEM

RELATED APPLICATION

The present application claims the benefit of U.S. Provisional Application No. 62/913,883 filed Oct. 11, 2019, which is hereby incorporated herein in its entirety by reference.

This invention was made with Government support under contract number W81WH-18-C-0361 awarded by the Defense Health Agency. The Government has certain rights in the invention.

Commonly Owned Applications

U.S. patent application Ser. No. 13/961,422, filed Aug. 7, 2013 and entitled Method and Device for Simultaneously Documenting and Treating Tension Pneumothorax and/or Hemothorax; U.S. patent application Ser. No. 14/581,339, filed Dec. 23, 2014 entitled Percutaneous Channel System and Method; U.S. patent application Ser. No. 16/113,707, filed Aug. 27, 2018 and titled Percutaneous Access Pathway System; and U.S. Patent Application Ser. No. 62/643,846, filed Mar. 18, 2019 and titled Systems and Methods Relating to Medical Applications of Synthetic Polymer Formulations, are hereby incorporated by reference herein in their entirety.

FIELD OF THE INVENTION

The present disclosure relates generally to the field of medical devices, and more particularly, to devices and methods for forming and/or maintaining a percutaneous access pathway in a patient's body.

BACKGROUND OF THE INVENTION

A wide variety of diagnostic and therapeutic procedures involve the introduction of a device through a natural or artificially created percutaneous access pathway in a body of a patient. One of the general objectives of access systems developed for this purpose is to minimize the introduction of infectious organisms from the skin or external environment into the body, while allowing for diagnostic and/or therapeutic procedures that require access into the body.

Establishing intracranial access (i.e. opening the scalp and drilling through the cranium) is an example of one type of procedure that requires an artificially created pathway. At the simplest level, this procedure is called trepanning (i.e. creating a burr hole or craniostomy), which is essentially the surgical placement of a relatively small hole in the cranium, typically achieved by using a surgical drill. Depending upon medical need, such holes may be sufficient for treatment (e.g. drainage of epidural blood) or may be used to facilitate further procedures and/or surgery (e.g. dural puncture, intracranial pressure monitoring, intracranial oxygen monitoring, ventriculostomy, external ventricular drain placement, intracranial hemorrhage drainage, other ventricular shunt, endoscopic surgery).

A number of devices and methods for establishing an intracranial access pathway are disclosed in the prior art for establishing such an access pathway, either through a burr hole or larger craniotomy procedure, which forms the basis for most neurosurgical procedures. However, existing methods are tailored to performance in a sterile operating room, as is typical for traditional neurosurgery, thus requiring a large sterile field that makes such procedures difficult to perform outside of the operating room (e.g. in the battlefield, out-of-hospital arena, emergency department, intensive care unit), while likely increasing infection risk when performed in such inherently non-sterile settings.

Traumatic Brain Injury (TBI) is of key concern to military medicine, accounting for up to one-fourth of Joint Theater Trauma Registry reviewed combat casualties. Prevention of secondary injury after brain insult is the guiding principal of modern TBI care, which needs to begin as soon as possible after injury to prevent additional tissue death. Among patients with moderate-to-severe TBI, extra-axial intracranial hemorrhage (e.g. epidural and subdural bleeding) may be immediately life-threatening. Epidural hematomas are known to rapidly accumulate between the skull and the brain's dura matter, which can quickly lead to brain herniation and death unless there is emergent neurosurgical intervention. As such, rapid intracranial access, for ICP monitoring and its reduction are the evidence-based standard of higher-level neuro-intensive care for many moderate-to-severe TBI patients. This includes the rapid drainage of extra-axial blood, intraparenchymal pressure monitoring, and ventricular CSF monitoring and drainage.

However, despite this immediate and life-threatening need, there are currently no neurosurgical interventions available to first responders (e.g. medics and corpsmen) in the far-forward environment. Additionally, even when reaching the next echelon of military or civilian care (e.g. an emergency department), neurosurgeon availability is a frequent problem. Domestically, the absence of neurosurgical subspecialty care has been declared a public health crisis in both rural and urban areas, while an even worse problem globally. One civilian study from a tertiary facility in Chicago showed that it took an average of over 5 hours (range up to 20 hours) to receive transfers of patients needing a neurosurgeon from facilities without them, with a decline in Glasgow Coma Scale score seen in many cases. For the military, there are also frequent operational delays to higher-echelon neurosurgical care. Force 2025 additionally predicts combat scenarios where evacuation time is significantly longer, requiring the forward movement of advanced capabilities for Prolonged Field Care (PFC).

While there are several possible medical interventions to attempt to decrease ICP (e.g. hyperventilation, mannitol, hypertonic saline), in practice these tend to offer only minimal or transient effect. As such, definitive ICP control frequently requires emergent surgical intervention to prevent secondary brain injury from causing worsened morbidity and mortality. The need to rapidly decompress the cranium has led to the concept of Damage Control Neurosurgery, similar to its better-known cousin of standard Damage Control Surgery (DCS) that is typically focused on non-neurologic surgical interventions. Under this paradigm, a neurosurgeon emergently takes the patient to the operating room to evacuate extra-axial hematoma or perform a ventriculostomy. Following the Monro-Kellie Doctrine, removal of extra-axial blood or ventricular CSF decreases volume within the skull to reduce ICP. As stated by Rosenfeld, "Although military triage may classify a severe head injury as being unsalvageable, a young fit soldier with a closed head injury may have their life saved by the timely evacuation of an intracranial hematoma in a forward facility." This is supported by evidence that, for extra-axial hemorrhage, reducing the time (less than 90 minutes) from severe clinical symptoms (e.g. anisocoria) to surgery is associated with significantly improved outcomes. Similarly, evidence-based research shows that ventriculostomy produces a sustained ICP reduction and related physiological improvements in over half of all patients in which it is used.

Although, in the setting of extra-axial hemorrhage without neurosurgical availability, it is within the scope of care for non-neurosurgeons (e.g. emergency physicians, general surgeons) to perform an emergency craniotomy (i.e. burr hole), in practice this is quite rare. This is primarily because non-neurosurgeons are uncomfortable with the traditional open neurosurgical technique, which has "created a therapeutic vacuum for patients remote from specialist care who meet the criteria for urgent burr hole drainage." Additionally, no devices have been simplified for use by medics, corpsman, physicians, or other providers in the forward environment, in which wide sterile field setup is impractical.

The traditional neurosurgical method for establishing intracranial access through the skull is to use a perforator drill-bit with a clutch mechanism to penetrate the skull. This requires the sterile setup of an operating room, with an open surgical approach first incising and retracting the overlying skin before dissecting down to the skull. From there, the operator uses a special drill to penetrate the exposed skull. The drill's clutch mechanism allows the bit to penetrate the bone, but automatically disengages upon skull penetration to make the procedure safer, by minimizing the risk of equipment "plunging" that would cause iatrogenic injury to the underlying brain. If inserting an intraparenchymal or other ICP monitor or performing a ventriculostomy, the surgeon subsequently advances by hand a tube into the brain.

Unfortunately, the combination of poor neurosurgical availability, especially in battlefield and rural areas, along with the technical difficulty of current neurosurgical procedures results in delays and missed opportunities for intracranial pressure monitoring and decompression. This is because the traditional procedures are optimized for a neurosurgeon working in an operating room, neither of which may be available in such settings. For example, the traditional clutch drill-bit requires an open approach, which is technically difficult and different from other procedures typically performed by medics and other non-neurosurgeon providers, while also requiring extensive bulky and frequently unavailable neurosurgical accessory tools for optimal performance. Thus, it is technically difficult to perform even the simplest of neurosurgery in such settings (e.g. burr hole placement, epidural drainage, ICP monitor placement, external ventricular drain placement). Additionally, any inserted components (e.g. drain, intraparenchymal monitor, other monitor, ventriculostomy tubing) are a source of infection, both upon insertion and later use, including need for repositioning.

Similarly, there are a wide range of procedures that may be performed via minimally invasive intracranial endoscopic neurosurgery that can benefit patients. However, these procedures are primarily performed in an operating room that maintains functional sterility externally around the patient while the surgeon is dressed in sterile attire (e.g. sterile gloves, gown). Sterile equipment (e.g. endoscope) is thus handled by the surgeon in full sterile attire before placement through a surgical hole or port into the patient, during which the surgeon continues to manipulate it while wearing sterile protective gear. However, this traditional setup means that such procedures are less amenable to performance outside the operating room (e.g. emergency department, intensive care unit) where sterility of the operator and their equipment is more difficult to maintain. Additionally, if there is need for repeating the procedure or adjusting a drain or other device left within the patient, the patient must normally return to the operating room where a full sterile setup is reestablished.

The literature discloses various additional known methods and devices for forming and/or maintaining an intracranial access pathway.

For example, U.S. Pat. Pub. No. 2015/0366620 to Cameron et al. describes the typical performance of sterile operator suite neurosurgery, which is not possible or is difficult to perform outside of an operating room (e.g. in the intensive care unit, emergency department, out-of-hospital).

The prior art also describes many variations on a traditional perforator drill-bit with a clutch mechanism for traditional burr hole drainage. This includes U.S. Pat. Pub. Nos. 2007/0270771 A1 to Ralph et al. that describes a craniostomy drill that sucks and saves bone chips; 2008/0281343 A1 to Dewey et al that includes a Surgical drill with hollow drive shaft that provides irrigation; 9,155,555 B2 to O'Brien, II that provides suction down its middle; 2010/0034605 A1 to Huckins et al. for a trephination drill for drilling holes in discrete controlled increments; and, 2004/0034382 A1 to Thomas that describes a trephination tool to allow better discrimination of a tangent plane. Additionally, U.S. Pat. No. 5,207,681 to Ghadjar et al. describes a drill guide apparatus for perpendicular perforation of the cranium. However, none of these drills leave in place a sealable port for repeat percutaneous access.

The prior art also describes many variations on systems to access and perform surgery upon, drain, or otherwise influence the intracranial space. This includes U.S. Pat. No. 9,211,163 B1 to Jaramaz et al that describes an apparatus for minimally invasive intracranial hematoma evacuation; U.S. Pat. No. 8,679,088 B2 to Abrahams that describes an intracranial hematoma removal surgical device; U.S. Pat. Nos. 9,161,820 B2, 9,770,261 B2, and 2019/0117254 to Mark et al. that provide a stereotactic brain surgery device; 8,403,878 B2 to Branch, Jr. et al. that describes a subdural drainage catheter with flow restoration mechanism; and, 2017/0197017 A1 to Martin that describes an irrigating suction cannula for removal of intracerebral hemorrhage. Similarly, U.S. Pat. Nos. 6,923,799 B1, 7,553,290 B1, and 7,694,821 B1 to Asfora describe a subdural evacuation system with drain and aspiration system. However, none of these describe a device optimized for use in the non-operating room setting to provide repeat percutaneous access to the intracranial space.

Finally, U.S. Pat. No. 5,891,100 to Fleckenstein provides a securing device for brain scan probes via a cranial screw with a pinch seal inside a sterile enclosure that allows for longitudinal movement. However, it is inserted via a traditional neurosurgical drill and does not contain a non-pierceable door that remains in its closed position when an attachment is not in place.

Regardless of use, the percutaneous access devices and methods of the art have not before provided for an optimized device for providing intracranial access in a minimally-invasive manner that is optimized for use outside the sterile operating room. As such, there is a need for a device and method to do so.

Each of the patents and published patent applications mentioned above are hereby incorporated by reference.

SUMMARY OF THE INVENTION

The present invention overcomes and substantially alleviates the deficiencies in the prior art by providing improved devices and methods for forming and/or maintaining a percutaneous access pathway. Under various embodiments, the initial percutaneous access pathway is formed via different methods and devices, which include the aforementioned techniques noted as background of the present invention that have been incorporated by reference. The provided assembly substantially reduces the possibility of iatrogenic infection while accessing and/or re-accessing a body space.

Under many embodiments, the percutaneous access pathway is provided by an auto-stopping mechanism, similar to that described under related applications (see prior section), but in this case being propelled by a drill that causes at least part of the device to spin. The distal tip of the drill-bit entering into a body cavity (e.g. the cranium) automatically triggers an auto-stopping mechanism that prevents further distal movement into the body (e.g. "plunging" into brain tissue). The drill can be either a specialized drill only for this application or one or more existing medical drills well known in the art (e.g. traditional hand crank drill, traditional plug-in drill, battery operated EZ-IO drill for intraosseous access placement). Additionally, in several embodiments, in contrast to current practice wherein the drill itself is typically sterile, by being cautious not to touch the distal "sterile" tip of the device, a user may utilize a non-sterile drill attaching to the proximal portion of the device to insert the device into the body. In some embodiments, rotational force is not supplied by an external drill, but rather from a drilling mechanism incorporated into the device itself (e.g. drill or drill components thereof incorporated directly into the device itself).

In many embodiments, the access pathway device additionally includes a component for reversibly or irreversibly connecting to one or more attachment devices (e.g. serially). In many of these embodiments, such a connecting component is a luer lock, while in others it is one of the many other medical connectors well known in the art (e.g. Y, barbed, stepped, bayonet, cross, compression, elbow, flare, funnel, giant-bore, large-bore, ISO 80369-3 ENFit®, ISO 80369-6 NRFit™, non-threaded, panel mount, pipe thread, quick disconnect, shielded, suction, T). In many of these embodiments, the device initially has a cap or other sealing mechanism on the connecting component, which is removed during use to allow connection to an attachment device. Such removal allows entrance to a pathway within the access device that ends within a body cavity when in use, which the cap or other sealing mechanism can reversibly block, thus preventing air and/or infection from entering the body cavity when in its closed position. In many of these embodiments, this cap or other sealing mechanism is airtight and in many it is non-pierceable. In many of these embodiments, the cap or other sealing mechanism prevents easy access to an internally sterile space within the access pathway device while in place.

In many embodiments, the connecting component is a port that allows a serial, reversible connection to one or more attachment devices. The port allows entrance to a pathway within the device that ends within a body cavity when in use, which the non-pierceable port can reversibly block, thus preventing air and/or infection from entering the body cavity when in its closed position. This contrasts with a traditional seal that is meant to secure equipment (e.g. pinch seal) or prevent air movement, as the port when closed cannot be easily pierced and is securely closed (e.g. prevents air movement). In many embodiments, the port can only be opened when a device attachment is in place and can only be removed once any inserted portion of the attachment is removed, thus maintaining a functionally sterile space within the body. In some embodiments, this port additionally incudes a lock that is automatically unlocked when an attachment is in place to further secure it from opening when a device attachment is not in place.

In many embodiments, the access pathway port contains a mobile pathway (e.g. through a cylinder, sphere, ball, ball-valve mechanism), valve (e.g. ball-valve mechanism), door, and/or tumbler that moves (e.g. rotates, slides) to block or allow access to the internal pathway and thus body cavity. In some embodiments, movement of the mechanism is caused manually by the operator (e.g. button, lever, switch, knob) and in others is caused automatically by connection of an attachment device to the port. In many embodiments, the access pathway port when in its closed position is lockable in a manner to prevent easy opening when an attachment is not connected. In many embodiments, the access pathway port when in its closed position is not easily pierceable. However, in some embodiments the access pathway port, attachment, and/or catheter does contain one or more additional pierceable barriers (e.g. duckbill valve, rubber, film, stopper) to keep air in or out of the body when the port is open.

In many embodiments, only the connection of an attachment device to the access pathway port allows the access pathway port to open, thus preventing air and/or infectious material from entering the port and body when an attachment device is not attached. In these embodiments, the attachment device thus functions as a key to open the locked port. When the access pathway port is closed, it is automatically or manually locked so that it cannot be easily opened without connection to an attachment device. Additionally, when closed, the port cannot easily be pierced, unlike a typical trocar seal.

In many embodiments, the proximal portion of the closed port is easily cleanable by swab, liquid, or other means, so that the portion that will connect to an attachment device may become functionally sterilized before doing so (e.g. if the port has been exposed to a non-sterile environment). For example, in many embodiments, the device forms a system of components that maybe interchanged, with multiple attachments that can connect to an inserted port. When the user first places the access pathway device, it is fully sterile from its packaging and an attachment can be immediately connected at that time. Should the user later remove that attachment, the patient may have only the access pathway device in for some time. Afterwards, the external portion of the access pathway device (e.g. port) may be contaminated. If there is need for reconnection of a new attachment (e.g. switching from a drainage attachment to one for intracranial pressure monitoring), then some or all of the external portion of the access pathway device may easily be sterilized (e.g. swabbed) before a new attachment is connected.

In many embodiments, when the access pathway device is connected to an attachment, the device allows a direct connection from a body cavity of interest, through the access pathway device, to the attachment device. In some embodiments, at least part of the attachment device (e.g. internal equipment component) then enters the body through the access pathway device via the established and open access pathway.

Many of the embodiments of the present invention contain one or more attachment devices that can connect to the access pathway device. In many embodiments, the device includes a system that includes a universal connecting component that can serially connect to multiple different types of attachment devices, each with its own utility and purpose (e.g. each with different internal equipment components). Thus, after universal access pathway device placement, the user can connect to it and exchange one or more different attachment devices, depending on clinical need, without having to exchange the access pathway device.

In some embodiments, an attachment device comes out of its packaging sterile and ready to be attached to the access pathway device. In others, an attachment device has a mechanism to prevent contamination of any surfaces that should remain functionally sterile during use (e.g. those that will be entering the body, those that could contaminate a component that will be entering the body) when the attachment is not connected to the access pathway device. In some embodiments, this prevention mechanism is a cap that can be removed from the distal end of the attachment device before connection to the access pathway device. In other embodiments, this prevention mechanism is disengaged manually by the operator manipulating a mechanism on the attachment device (e.g. via a button, lever, switch) that removes a barrier before, during, and/or after connecting the attachment device to the access pathway device. In some embodiments, this prevention mechanism is removed automatically by connection of the attachment device to the access pathway device and/or insertion of part of the attachment device (e.g. internal equipment component). In some embodiments, the mechanism to remove this prevention mechanism is combined with or related to a mechanism for opening the connecting component itself. In some embodiments, this prevention mechanism is irreversible (e.g. foil cap removal) and in others it is reversible (e.g. movable door).

In many embodiments, one or more attachment devices contain an external sheath to protect at least part of an internal equipment component from the external (e.g. non-sterile) environment. In some of these embodiments, the sheath is formed of flexible tubing (e.g. plastic), collapsible or foldable material (e.g. corrugated tubing), and/or bag or bag-like material (e.g. plastic bag, plastic tubing). In many of these embodiments, the internal equipment component of the attachment device can be inserted, manipulated, and/or removed by the operator while the outer sheath maintains a barrier (e.g. functionally sterile partition) between the portion of the internal equipment component device that will enter the body and the user. In many embodiments, the sheath is clear or at least partially transparent, to allow for visualization of the equipment within.

In many embodiments, the attachment device can additionally be connected to external hookups that are standard for that device type. For example, in embodiments wherein the internal equipment component of the attachment is an intracranial pressure monitor, the proximal attachment device end allows a functional connection to a pressure measuring apparatus. For another example, in embodiments wherein the internal equipment component of the attachment is ventriculostomy tube, the proximal attachment device end allows a functional connection to ventricular drain monitoring and/or draining equipment. For another example, in embodiments wherein the internal equipment component of the attachment is hematoma drain (e.g. epidural, subdural, intracerebral), the proximal attachment device end allows a functional connection to suction or drainage (e.g. see Asfora's subdural evacuation system previously described). Under many embodiments, the attachment device additionally includes luer lock or other connectors, well known in the art, to allow connection to other medical devices (e.g. 3-way stop cock allowing syringe connection).

The internal equipment component of the attachment device varies by embodiment with neurosurgical equipment examples including: ventriculostomy tube, intracranial pressure monitor (e.g. intraparenchymal, epidural), intracranial oxygen monitor, external ventricular drain, device to drain intracranial hemorrhage, other ventricular shunt, surgical equipment, endoscope, irrigation, suction, irrigation and suction, mechanical agitator, and/or other surgical instrument. Under various embodiments, the internal equipment component is a conventional, endoscopic, and/or robotic surgical instruments (e.g. one or more single-port access surgery devices, cutters, forceps, scissors, staplers, probes, dissectors, hooks, retractors, sponge-holding forceps, biopsy forceps, biopsy cannulas, staple-transection devices, electric knifes; suction devices, sutures, and/or retractors).

By way of exemplification, in one embodiment, the device is utilized to emergently treat an epidural hematoma in a trauma patient. After identifying the location of the bleeding, the user utilizes an existing medical drill (e.g. the EZ-IO drill) to cause the drill-bit to enter the cranium, where the drill-bit automatically halts further forward movement to prevent injury to deeper brain tissue. The user then either causes blood from the internal space to drain through the device (e.g. through removal of a portion of the access pathway device) or assembles it such that an attachment can be placed to allow and/or encourage blood drainage. In the latter case, under one embodiment, the internal equipment component of the attachment device is be an epidural drain covered by a sheath over most of its length. This drain can then be advanced by the user through its outer covering into the desired location to optimally drain the epidural blood. Additionally, readjustment of placement can then later be performed without need for the user to become sterile, as the epidural drainage tube is covered by the protective outer sheath. It should be clear from this description that device embodiments include any standard drainage and/or surgical equipment that is amenable to being placed within a sheath and can be inserted through the access port. The invention is not limited to only an epidural drainage tube or the other internal equipment components set forth herein for purposes of exemplification. In many embodiments, one or more attachment devices of a full system have no sheath and/or internal equipment component. For example, in some embodiments the access pathway device reversibly connects to an attachment device that allows simple drainage from the body. Under some embodiments, there is a step and mechanism for dural puncture (e.g. to facilitate subdural, intraparenchymal, or ventricular placement).

In many embodiments, one or more attachment devices contain a reversible locking mechanism (e.g. equipment locking mechanism) to ensure that the internal equipment is not inserted into the body until the operator wishes it to do so and/or stays in the desired location once inserted in the body (e.g. holding a drainage tube at the desired length within the cranium). Under some embodiments, the equipment locking mechanism an O-ring, gasket, or other component that makes it more difficult to withdraw the internal equipment than it is to advance it or vise versa. Under some embodiments, the equipment locking mechanism is a piece of plastic with a hole cut out for a piece of equipment to move within that is biased (e.g. by spring, band, and/or its own material) to hold the internal equipment in place when not depressed, but allows it to move into or out of the patient when depressed. In other embodiments, the equipment locking mechanism is actuated by rotating the lock (e.g. pierce seal) and thus compressing one or more O-rings against a compression piece, causing the O-ring to hold internal equipment component in place. In some embodiments, an equipment locking mechanism utilizes other mechanisms to reversibly hold the internal equipment component at the desired position within the body such as, for example, a clamp, tie, hose clamp, screw/band clamp, worm gear, Jubilee Clip, Marman clamp, spring clamp, wire clamp, ear clamp, compression fitting, push-fit fitting, swage fitting, clamp fitting, crimp banding, and/or t-bold clamp. In some embodiments, the attachment device has no equipment locking mechanism.

In many embodiments, the device anchors, stabilizes, and/or secures the percutaneous access pathway to the body (e.g. via securing the access pathway port to the skin and/or deeper structures). Examples include through sutures, staples, glue, gum, hydrogel, and/or tape; tension from an expanded catheter within the body wall; adhesive that holds the catheter, port, and/or a larger stabilization pad onto the skin; and/or, expansion of one or more balloon(s) within the body cavity, within the percutaneous access pathway, and/or externally. In many embodiments, the aforementioned means provide the added benefit of preventing air and/or infection from entering the body from around the outside of the needle (e.g. through space between the outside of the needle and the surgical incision). In various embodiments, the access pathway device is anchored to make the percutaneous access pathway perpendicular to the skin, at a non-perpendicular angle (e.g. to facilitate tube placement or surgical access), and/or adjustable so as to allow movement to a desired angle.

Under some embodiments, the needle and/or stylet are stiff metallic tubes with cutting and/or grinding edges that are not readily deformable. However, in some embodiments the stylet is blunt and/or blunter than the needle. Examples of cutting and/or grinding edge embodiments include angled tips, tips with abrasive grit, tips with spaced teeth, and tips related to known art for cutting bone and/or other hard surfaces. In many embodiments, the stylet and/or the needle is structured to cut bone while minimizing damage or the chance of damage to underlying dura and/or skull cavity components.

Many of the embodiments additionally include an internal cutting component within the stylet to assist with skull penetration and prevent an internal core from clogging the stylet (e.g. either by assisting with drilling and/or chopping up the bone core or by allowing removal of the core with removal of the internal cutting component). Under many of these embodiments, the internal cutting component is removed after access to cranial space has been achieved. Under many of these embodiments, the internal cutting component is a stiff metallic tube with or without a distal cutting edge (e.g. trephine needle). One benefit of these embodiments is that such a distally hollow internal cutting component reduces the force necessary to drill through the skull while allowing for removal of the bone plug when the internal cutting component is removed, which prevents the bone plug from clogging the access pathway made through the stylet. Some embodiments allow and/or provide for suction through the internal cutting component. Some embodiments do not include an internal cutting component.

In some embodiments, the access pathway device is covered partially or fully with additional material(s) that can provide additional benefits when in contact with the body tissue. Examples include means to increase and/or decrease the cross-sectional area of the stylet; to reduce friction and/or the chances of tissue being pinched; to decrease the chances of infection (e.g. antimicrobial properties); to prevent clotting; and/or to have drug-releasing properties (e.g. anesthetic or other anti-pain medications). In some embodiments, there is an additional catheter outside the needle of the access pathway device, which in some embodiments is removable.

Under some embodiments, many of the access pathway device components are not present and a standalone port is placed directly into an incision into the body (e.g. into the cranium), with the port allowing access to the underlying potential or maintained pathway into the body.

In some embodiments, one device fits all patients. In others, part or all of the device is differently sized for different subgroups so that the appropriately sized device can be chosen for different subgroups based on, for example, weight, age, gender, length, pre-determined size categories (e.g. Broselow scale), and/or other indicators. For example under some system embodiments, the connecting component and portion of the attachment device that connect to it are universal, while the intracranial access device may come in more than one length and/or width (e.g. small, medium, large) and there are multiple different attachment device options and sizes (e.g. drainage tube diameters). This allows multiple attachment device to be used with a placed access device, but the user may choose different intracranial access device lengths based on the patient (e.g. patient size) and attachment based on clinical need (e.g. tube diameter size). Under various embodiments, differently sized components come together in a kit, with means for determining proper sizing.

Under different embodiments, different portions of the device are disposable and/or non-disposable. In some embodiments, the invention is inexpensively manufactured with all of it designed to be disposed of after a single use. Parts may be made of metal or plastic or other suitable material. Under many embodiments, the device is compatible and/or safe for use in an MRI environment. Under various embodiments, different parts are composed of a radio-opaque material and/or contain radio-opaque markers. Under various embodiments, the device may be packaged as a system with an intracranial access device, attachment device, and/or insertion equipment all coming together, while in others the device components (e.g. intracranial access device, attachment device) are packaged separately as individual units.

There have been illustrated and described herein methods and devices for forming and/or maintaining a percutaneous access pathway. While particular embodiments of the invention have been described, it is not intended that the invention be limited thereto, as it is intended that the invention be as broad in scope as the art will allow and that the specification be read likewise.

From the foregoing, it can be seen that the present invention provides an effective means for forming and/or maintaining a percutaneous access pathway within animals, especially humans. In various embodiments, the device is used to form and/or maintain a percutaneous access pathway into different body cavities. These include pathways into the cranium, as well as chest (e.g. pleural cavity, heart), abdomen, retroperitoneal, cranium, trachea, abscess, artery; bladder; bone; collection of fluid (e.g. empyema, ascites, pleural, other effusion); organ; skull, trachea; vein; vessel; and/or, other body cavity. Although the example of the cranium with the placement of a subsequent epidural drain has at times been used to illustrate the invention, it should not limit its scope as it could also similarly be used to insert other equipment and/or access other body cavities and/or spaces. The device can also similarly be used with any other surgical procedure where a reusable intracranial access device for repeat procedures and/or manipulation in a non-sterile environment would be of benefit.

Moreover, it should also be apparent that the device can be made in varying lengths, sizes and capacities, and the precise composition of the device may be varied appropriately to treat adults, children, and infants. While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification and that elements of certain embodiments can be combined with elements of other embodiments. Additional objects, advantages, and novel features of the invention will be set forth in the description which follows, and will become apparent to those skilled in the art upon examination of the following detailed description and figures. It should be understood that not all of the features described need be incorporated into a given system or method.

DETAILED DESCRIPTION OF THE INVENTION

Figure 1:
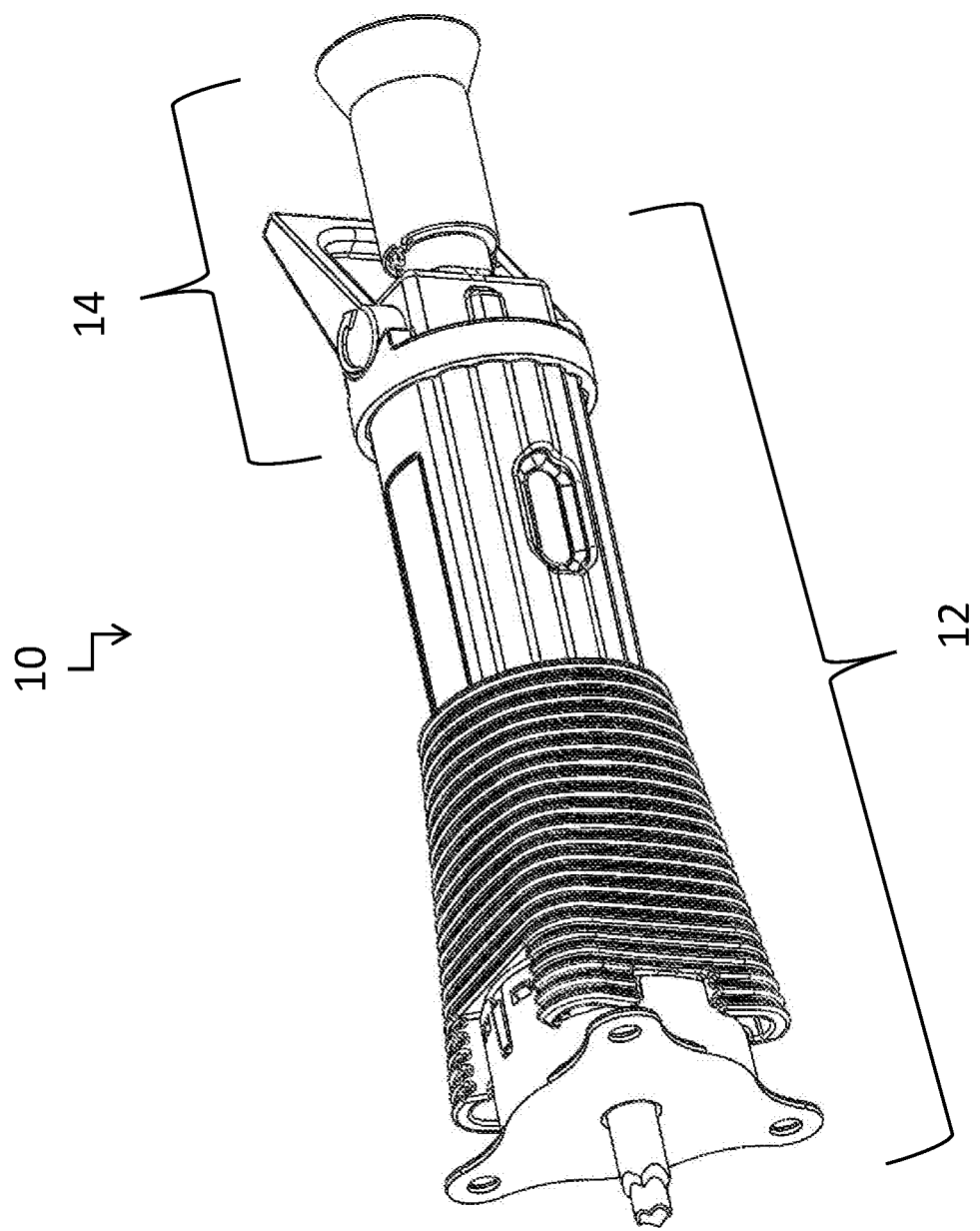
FIG. 1 is an isometric view of the access pathway in accordance with an embodiment of the invention, as assembled prior to use.

Referring to the drawings FIG. 1-19, embodiments of the present invention are illustrated. For ease of reference, distal shall refer to the end of the device farthest away from the user/operator, while proximal shall refer to the end of the device closest to the user/operator.

Figure 2:
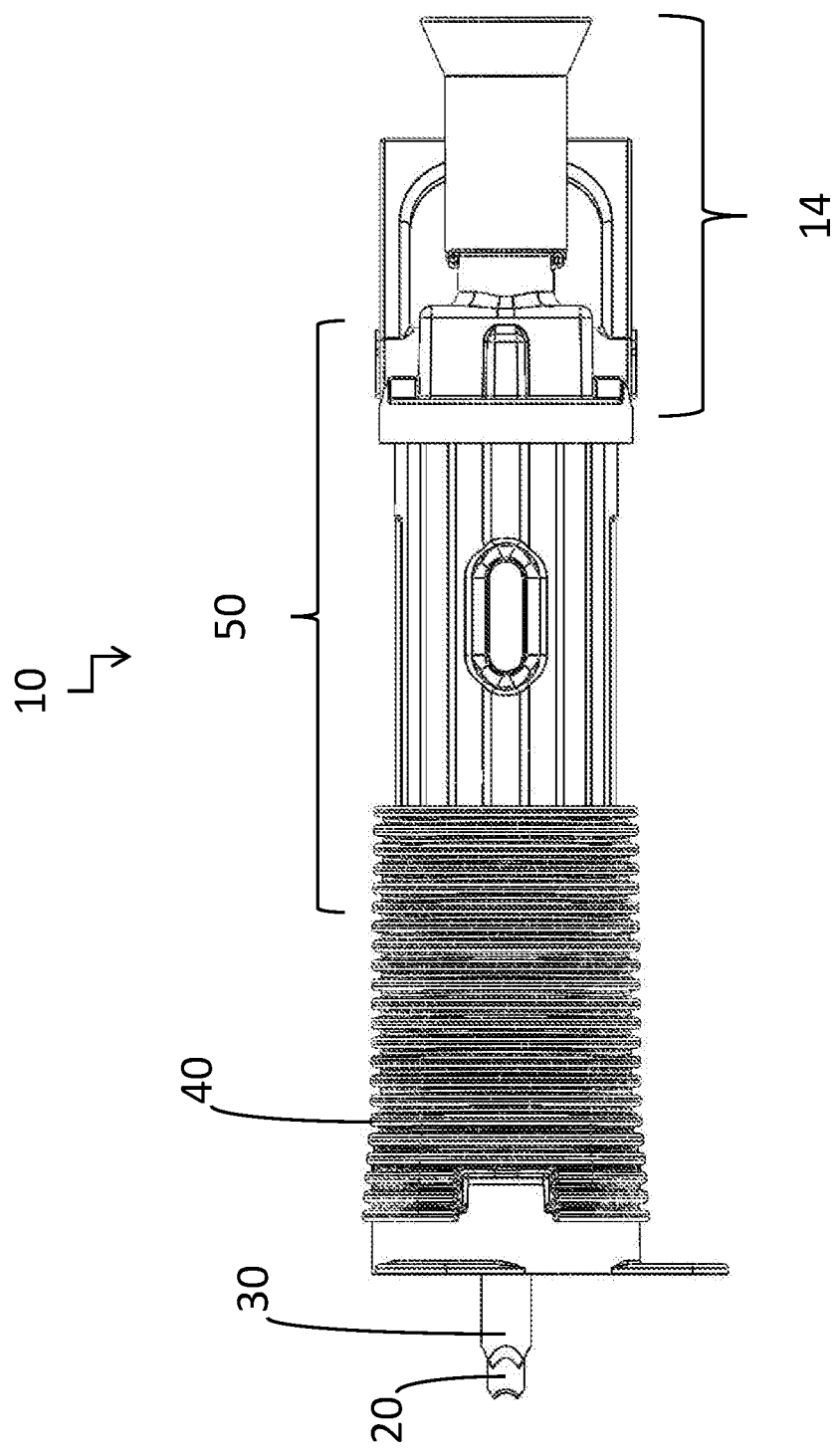
FIG. 2 is a side view of the access pathway in accordance with an embodiment of the invention, as assembled prior to use.
Figure 3:
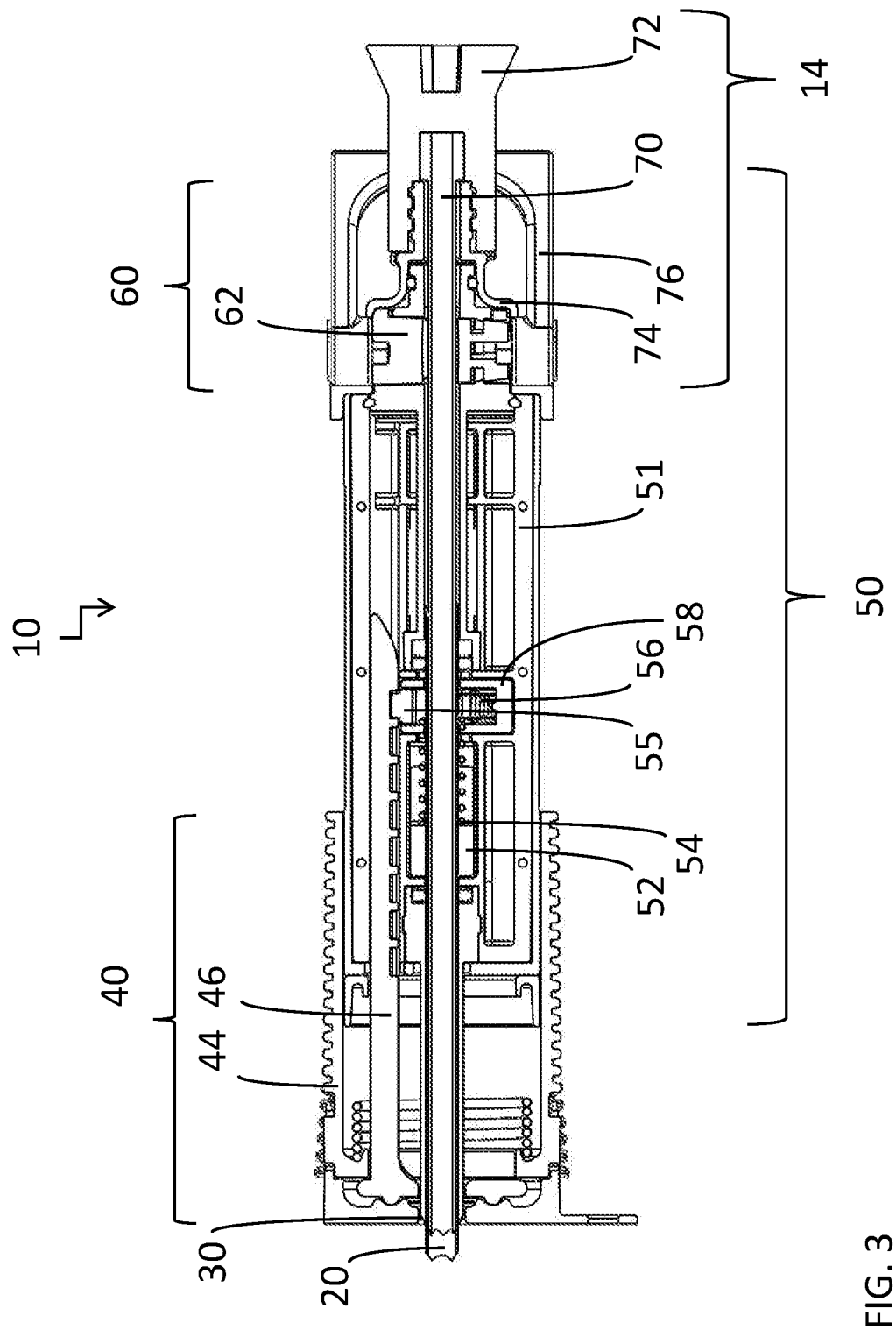
FIG. 3 is a cross-sectional view of the access pathway in accordance with an embodiment of the invention, as assembled prior to use.

FIGS. 1-3 show access pathway device 10 made up of intracranial access pathway device 12 and drive assembly 14 according to an embodiment. Intracranial access pathway device 12 is further composed of stylet 20, trephine needle 30, stabilizer 40, main body 50, and port 60, including port cylinder 62. Drive assembly 14 is further composed of internal cutting component 70, internal cutting component drive 72, drill cap 74, and lever 76. Stabilizer 40 is further composed of stabilizer case 44, and stabilizer rack 46. Main body 50 contains key 52, axial spring 54, lock 55, lock spring 56, and middle body 58, along with body case 51.

Figure 4:
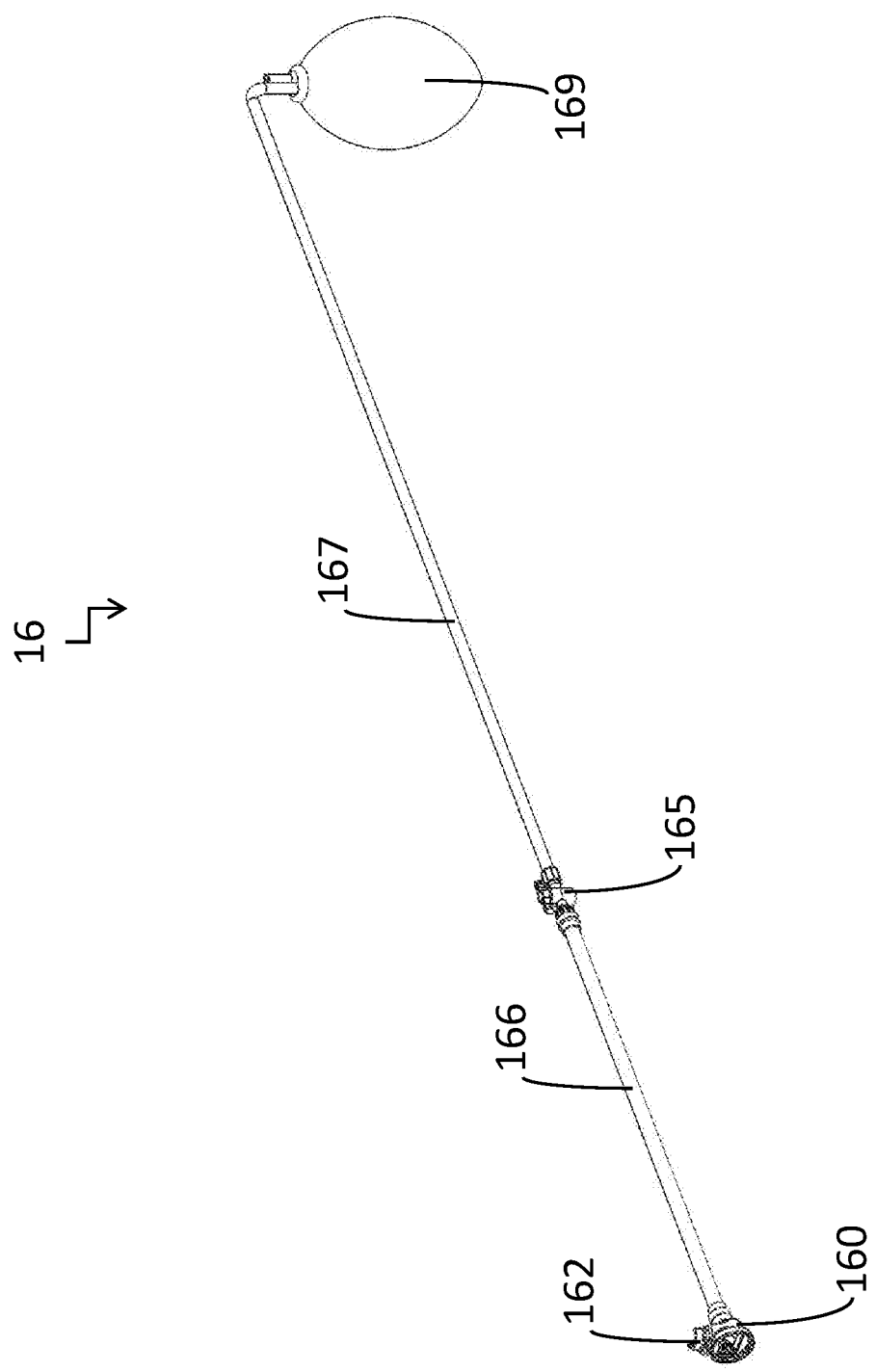
FIG. 4 is an isometric view of an attachment device containing a drain in accordance with an embodiment of the invention.
Figure 5:
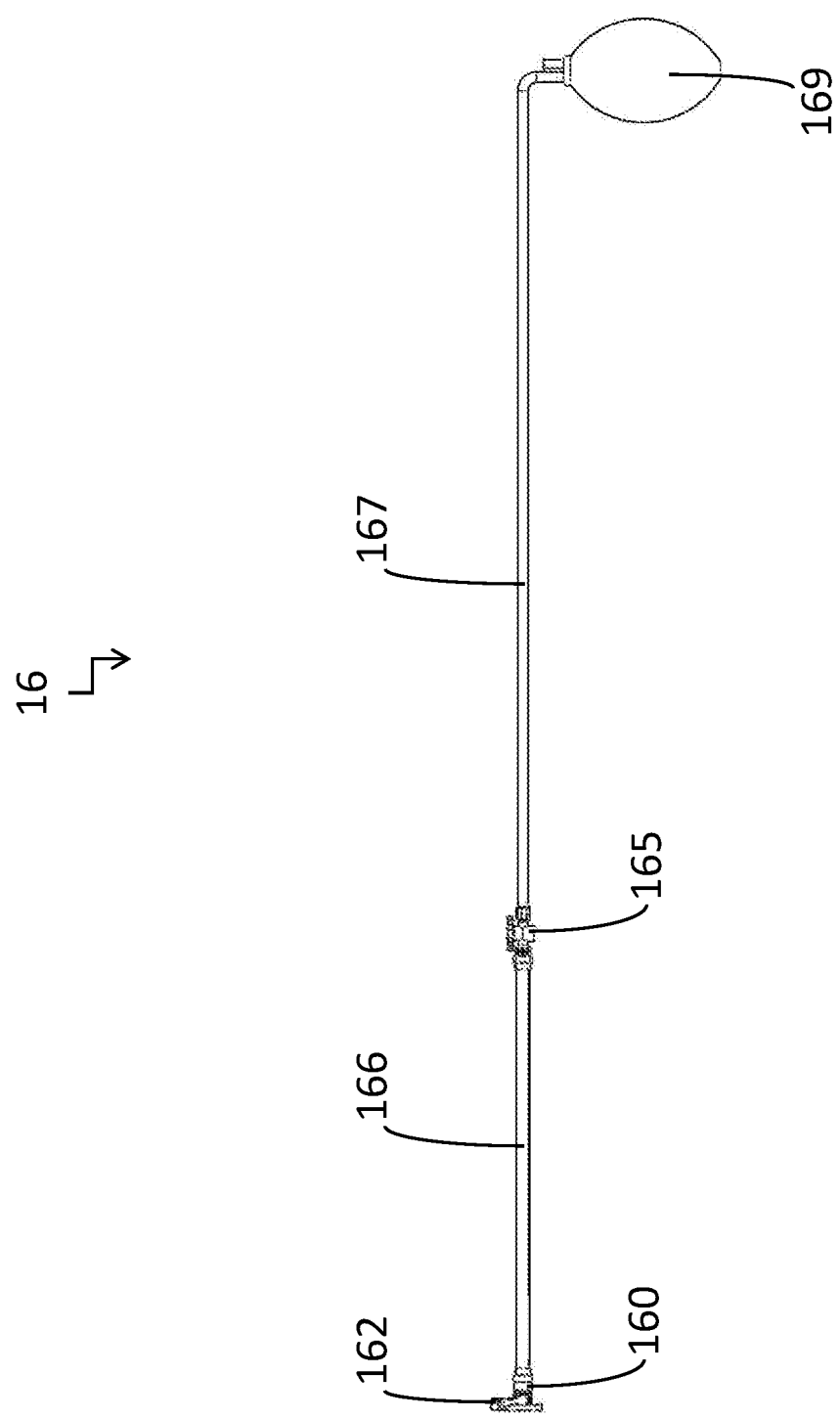
FIG. 5 is a side view of an attachment device containing a drain in accordance with an embodiment of the invention.
Figure 6:
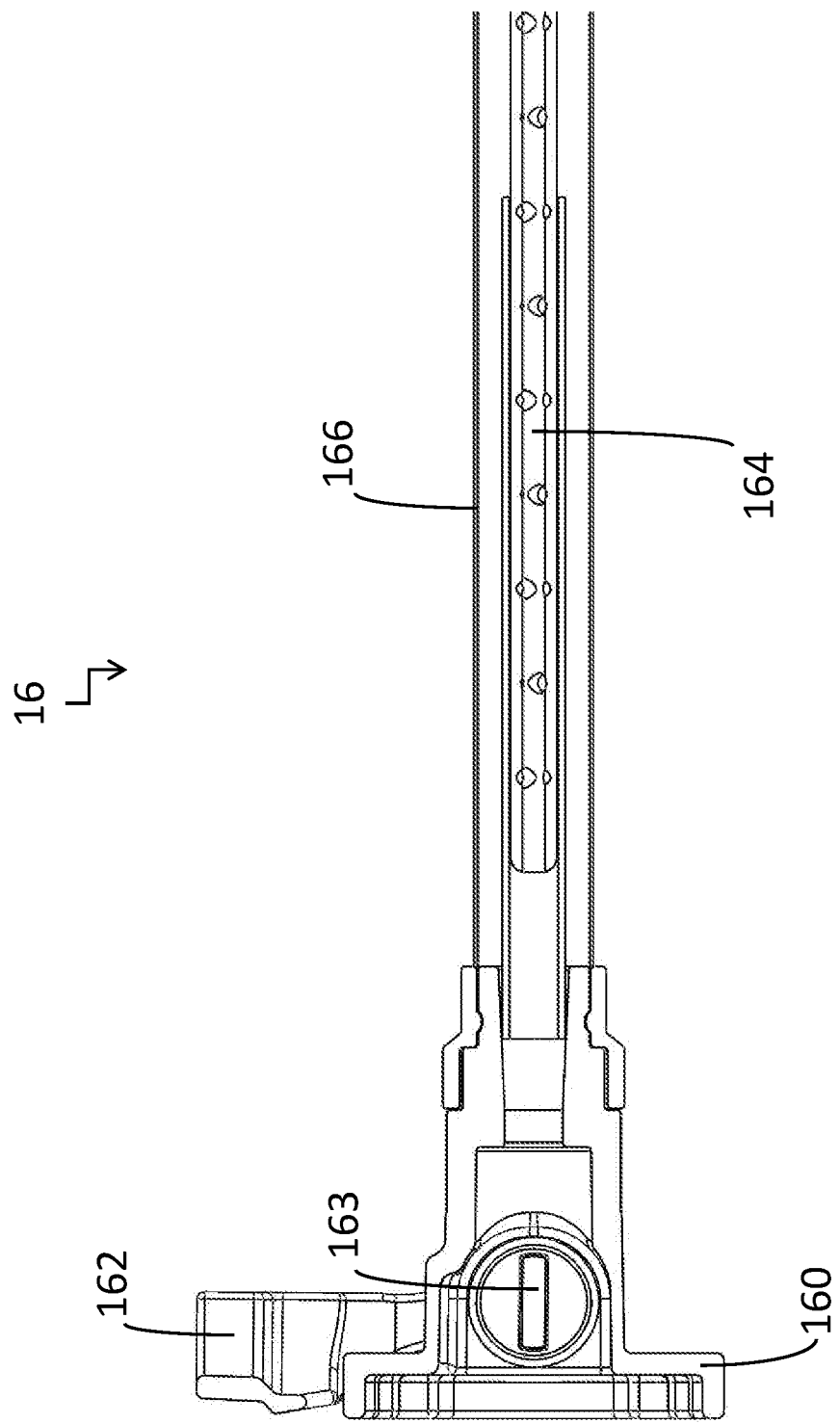
FIG. 6 is a cross-sectional view of an attachment device containing a drain in accordance with an embodiment of the invention.

Referring now to FIGS. 4-6, one embodiment of attachment 16 is shown. In this embodiment, an epidural drainage tube 164 is used as an example of an internal equipment component, connected to stopcock (165), tubing (167), and bulb suction (169). Attachment 16 includes attachment cap 160, lever 162, tube 164, and sheath 166. In some embodiments, there is additionally a reversible tube locking mechanism (not shown), to keep tube 164 from moving proximally or distally before and/or after use. Lever 162 is connected to key 163 and movement of the lever causes the movement of the key (i.e. in this embodiment, rotation of the lever causes the key to rotate). Tube 164 is at least partially covered by sheath 166 and sealed to it at connection point 168, but slides within sheath 166 and attachment cap 160 such that it can extend out of the cap if sheath 166 is collapsed by the operator. Under some embodiments, in initial configuration attachment 160 includes a removable cap (not shown) sealing its distal exit closed prior to use, which provides the benefit of enclosing an area within attachment 16 that maintains a barrier to the external environment.

Referring now to FIGS. 7-12, an embodiment of the invention is shown accessing a body cavity (e.g. skull cavity), wherein the device automatically senses entrance into the cavity and halts further distal movement to prevent plunging and injury to underlying organs (e.g. brain). Under this embodiment, stylet 20 is connected to key 52, such that they move together as one unit, and they are able to move proximally and distally within main body 50. Lock 55 is capable of perpendicular movement, to engage or disengage with stabilizer rack 46.

Figure 7:
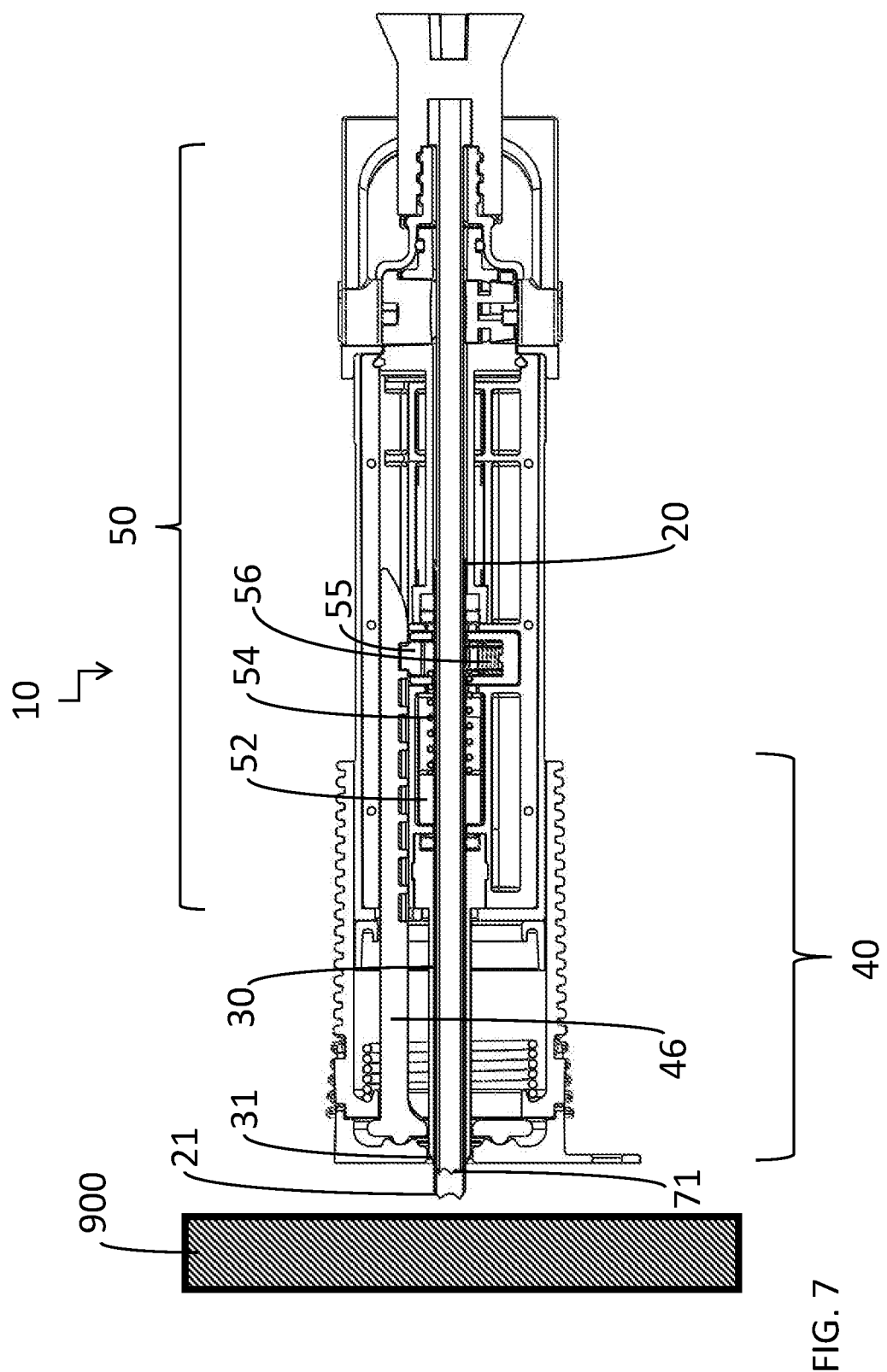
FIG. 7 is a cross-sectional side view of the access pathway in accordance with an embodiment of the invention, shown as assembled prior to insertion into a body cavity.

FIG. 7 shows access pathway device 10 prior to insertion through skull 900. Stabilizer 40 initially extends distally from main body 50 along the tract of trephine needle 30.

Spring 54 biases stylet 20 and key 52 to their distal position, with stylet tip 21 of stylet 20 protruding out distally past needle tip 31 of trephine needle 30 and internal cutting component tip 71. As lock 55 is not engaged with key 52 in this distal position, biased perpendicularly by locking spring 56, lock 55 is engaged with stabilizer rack 46, which inhibits the movement of stabilizer 40 in relation to the rest of device 10.

Figure 8:
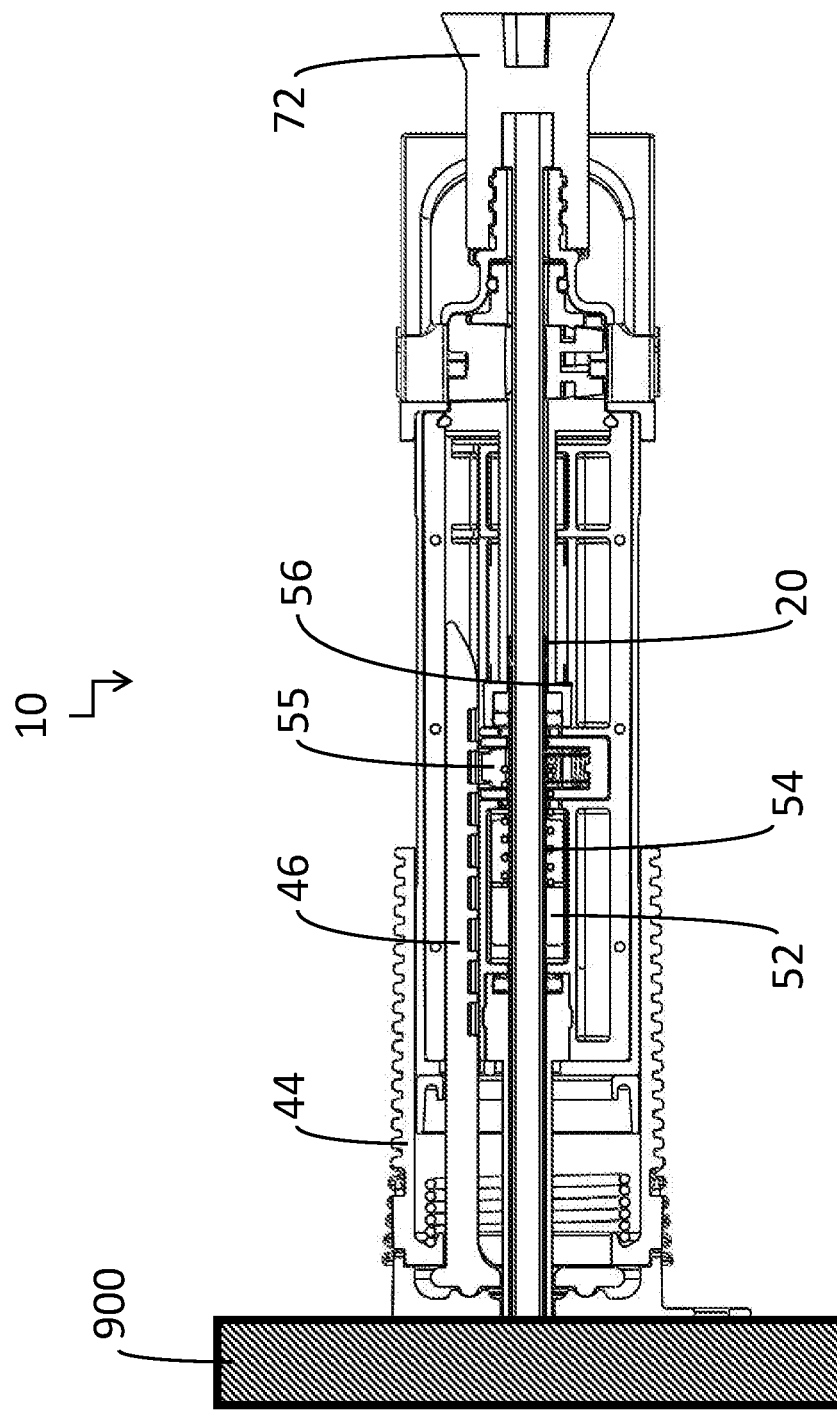
FIG. 8 is a cross-sectional side view of the access pathway in accordance with an embodiment of the invention, shown upon contact with the body (e.g. calvarium).

FIG. 8 shows access pathway device 10 upon contact with skull 900. To get through the overlying scalp tissue, the user can either make an incision (e.g. with a scalpel with or without further tissue dissection) or utilize the device itself to drill directly through the overlying tissue. To drive the device, the user connects a drill (not shown, but with many types well known within the art) to internal cutting component drive 72 at the proximal end of access pathway 10. This causes the device to spin, with the exception of stabilizer case 44, which can remain non-spinning on the patient and/or within the user's hand. Not shown, but in some embodiments, one or more stabilizer disks, ball bearings, or other low friction mechanisms provide a means for reducing friction between the spinning stabilizer rack 46 and non-spinning stabilizer case 44. When a user pushes the device onto skull 900 (or similarly overlying tissue, not shown) the countervailing force overcomes axial spring 54 and pushes stylet tip 21 (hidden in this image inside skull 900) proximally in reference to the rest of the device, which exposes internal cutting component tip 71 and trephine needle tip 31 for drilling (both also hidden in this image inside skull 900). This also causes stylet 20 and key 52 to move proximally in reference to middle body 50, which in turn causes key 52 to engage with lock 55 so that lock 55 becomes no longer in contact with stabilizer rack 46. Thus, when the device encounters resistance from skull 900, although stabilizer 40 is flush with skin and/or skull, it is mobile so that the device can drill distally into the body cavity.

Figure 9:
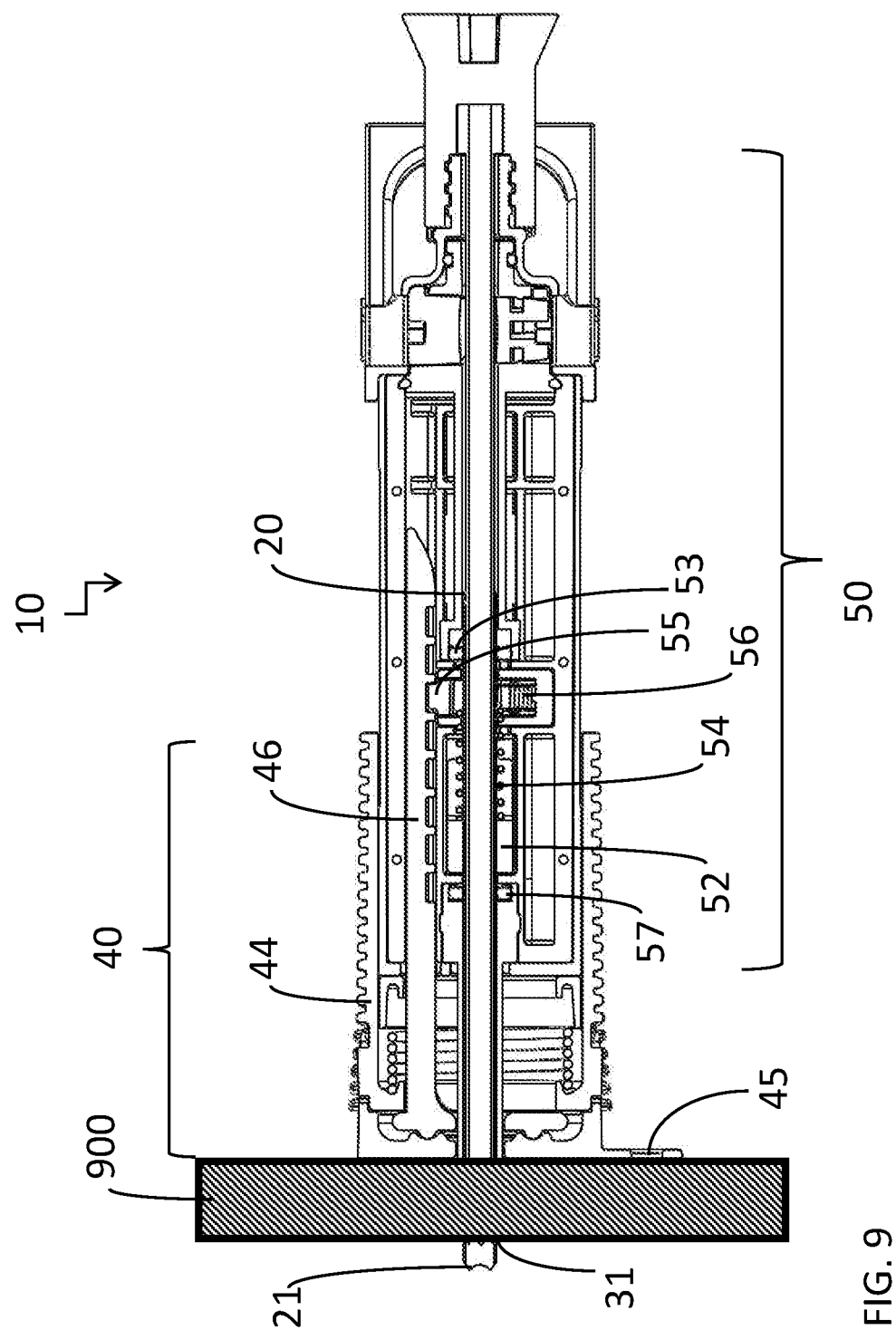
FIG. 9 is a cross-sectional side view of the access pathway in accordance with an embodiment of the invention, shown upon penetration into a body cavity (e.g. the skull cavity).

FIG. 9 shows access pathway 10 passing through skull 900 and into the skull cavity. Once stylet tip 21 and has reached the body cavity, spring 54 is free to move key 52 and thus stylet 20 distally in reference to needle tip 31. As key 52 moves distally in reference to main body 50, it disengages from lock 55, which (pushed by lock spring 56) then engages with stabilizer rack 46 to inhibit the movement of stabilizer 40 in relation to body 50. This, in turn, prevents needle tip 21 from moving further into the cavity, thus minimizing the chances of injuring distal vital structures. O-rings 53 and 57 provide proximal and distal airtight seals between stylet 20 and body 50. Thus, described is a mechanism for automatically halting the forward movement of an at least partially spinning device upon penetration into a body cavity, while simultaneously establishing a percutaneous pathway into said cavity.

The device having halted its forward motion, the drill (not shown) can then be removed from the proximal end of access pathway device 10. Once the distal end of stylet 20 is placed into the appropriate body cavity (e.g. cranial cavity), access pathway device 10 can be secured to the patient by one or more of the many means of adhering devices to patient skin known in the art (e.g. tape, glue, gum, suture, staples, adhesive, etc.). In some embodiments, access pathway device 10 contains a means for establishing an air-tight seal (e.g. adhesive, occlusive ointment) from access pathway device 10 (e.g. from stabilizer case 44) to the patient's skin. In some embodiments, eyelet(s) 45 on stabilizer case 44 are available to secure the device to the skin via suture and/or staples.

Figure 10:
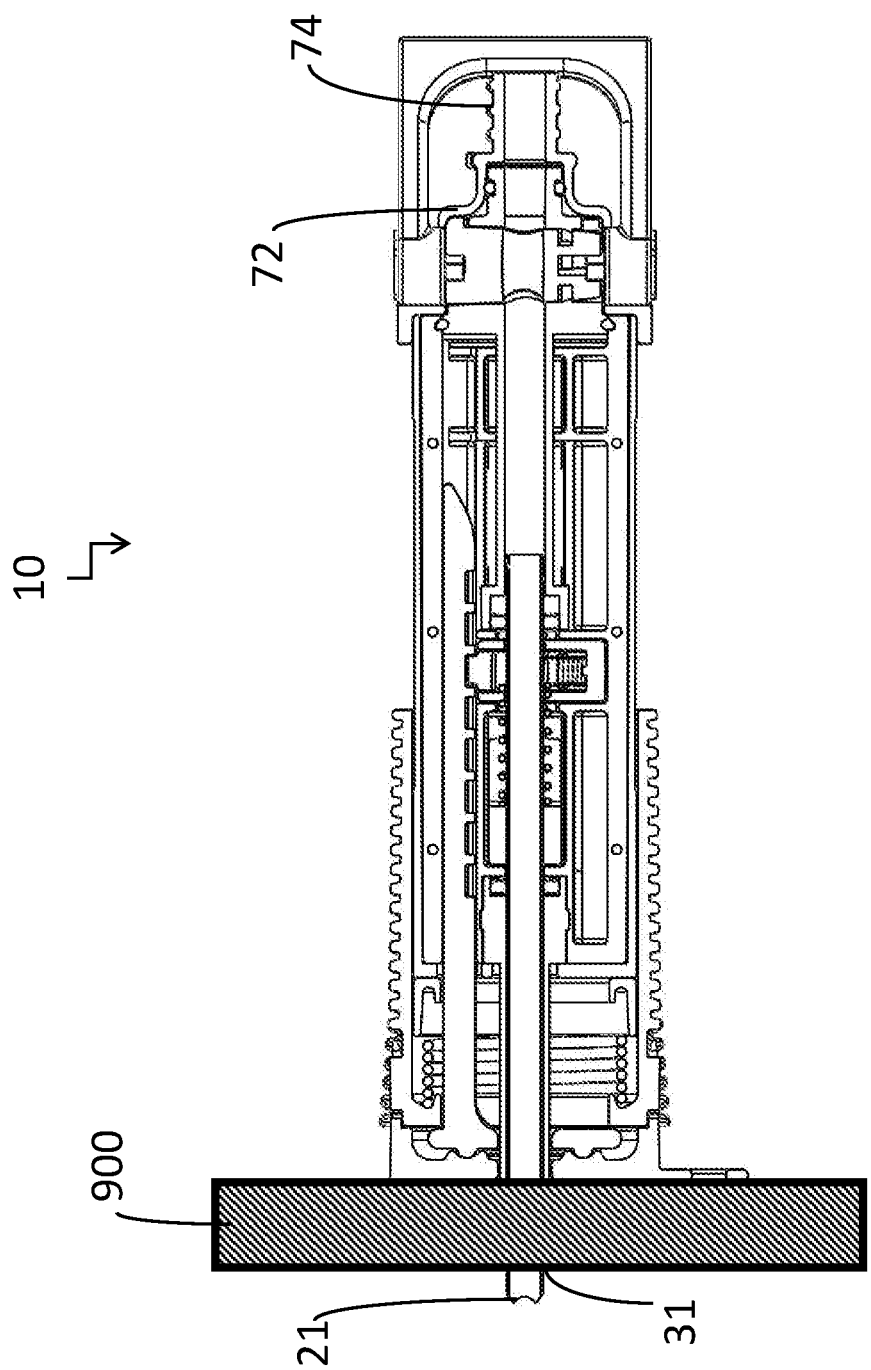
FIG. 10 is a cross-sectional side view of the access pathway in accordance with an embodiment of the invention, shown upon removal of drive assembly.

FIG. 10 shows access pathway device 10 through skull 900 into the skull cavity after removal of drive assembly 14 (now not shown). The device then provides a continuous internal pathway stretching through access pathway device 10 from its distal end in a body cavity (i.e. stylet tip 21) to its proximal portion in the external environment (i.e. drill cap 74). This pathway may allow blood or other fluid to drain and/or the insertion of other implements if so desired. Under some embodiments, drive assembly is attached to a sheath (e.g. between the distal portion of internal cutting component drive 72 to the proximal portion of drill cap 74) or sterile bag (neither shown), such that despite its removal the device always maintains a barrier between the external environment and internal accesses pathway.

Figure 11:
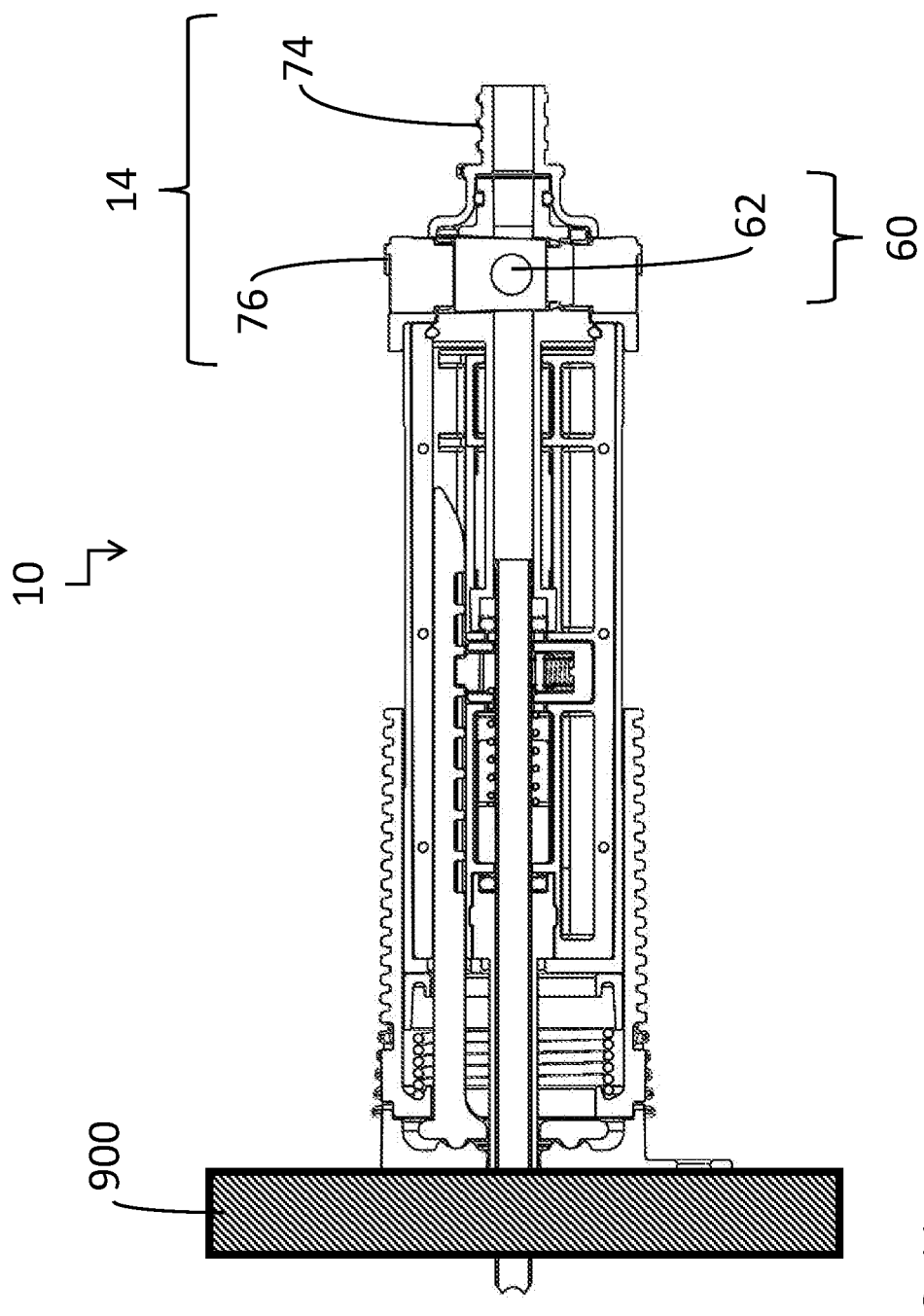
FIG. 11 is a cross-sectional side view of the access pathway in accordance with an embodiment of the invention, shown after port closure.

FIG. 11 shows access pathway device 10 through skull 900 into the skull cavity after movement of lever 76 to its closed position. As lever 76 is connected to key 163 (not shown) within drive assembly 14 that engages with port cylinder 62, its movement reversibly closes port 60, thus providing a secure barrier within access pathway 10 (i.e. between the external environment and the body cavity). In some embodiments, an airtight seal is formed directly between port cylinder 62 and port 60, while in others the seal is obtained and/or assisted by one or more pressure or non-pressure O-rings, seats, washers, lubricants, and/or gels. In many embodiments, the mechanism is a variation on a ball-valve mechanism. In some embodiments, port cylinder 62 is not a cylinder, but rather a ball or other mobile door type. Regardless, when in its closed configuration, port cylinder 62 prevents air or infection from entering the body through access pathway 10. Additionally, in many embodiments, the device prevents drill cap 74 from being removed from port 60 when lever 76 is in its open position (see FIG. 10), allowing removal only when it is in its closed position (shown in FIG. 11). Thus, the device automatically seals access pathway 10 before and/or during the removal of drill cap 74, to prevent entrance of functionally non-sterile material from the external environment into the body cavity.

Figure 12:
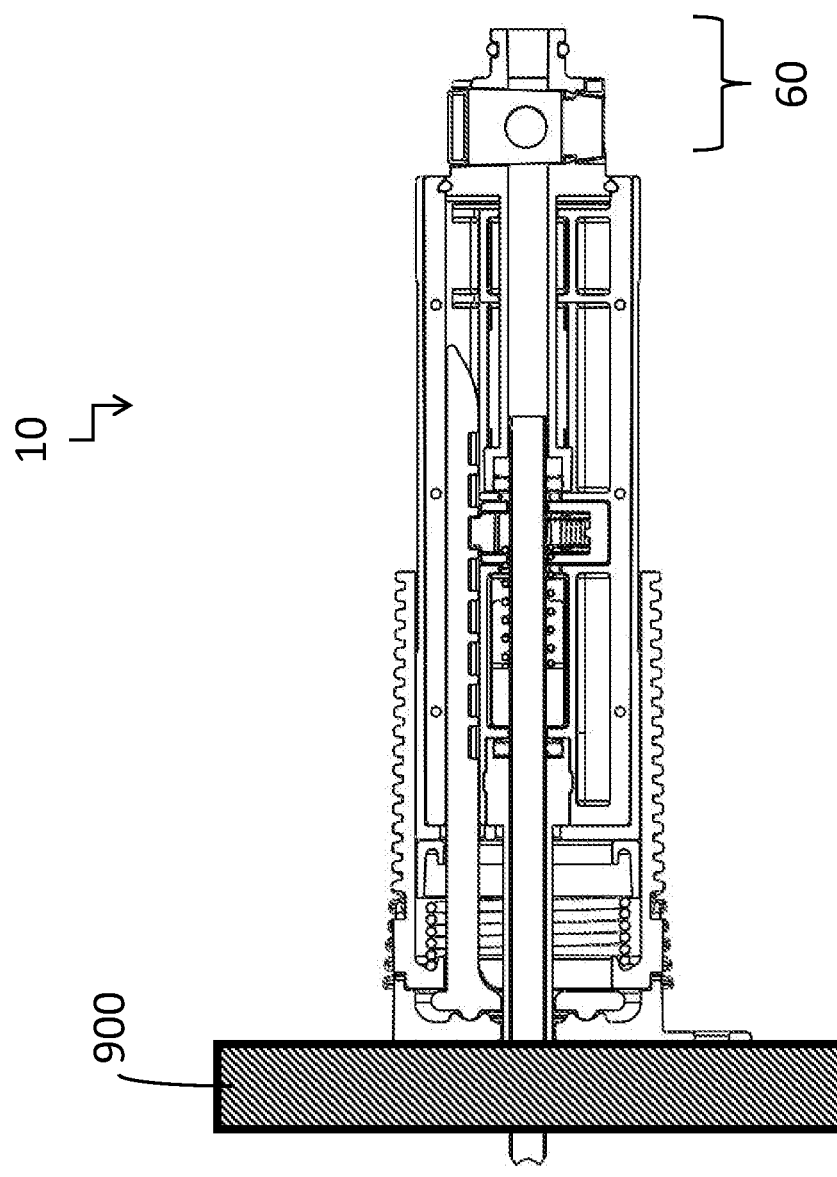
FIG. 12 is a cross-sectional side view of the access pathway in accordance with an embodiment of the invention, shown upon removal of attachment cap.
Figure 13A:
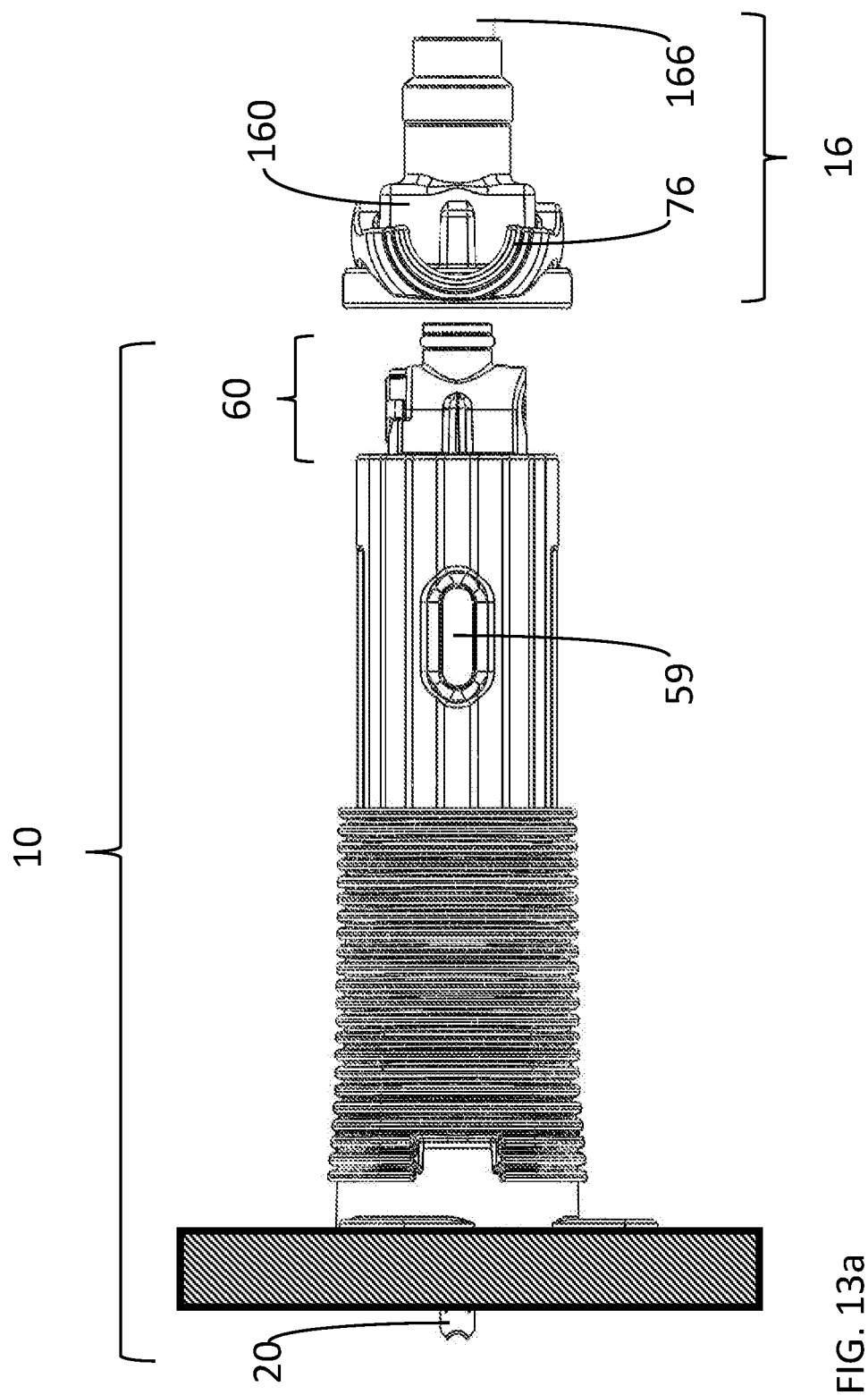
FIG. 13a is a cross-sectional side view of the access pathway and an attachment device in accordance with an embodiment of the present invention, shown prior to connection of the two components.
Figure 13B:
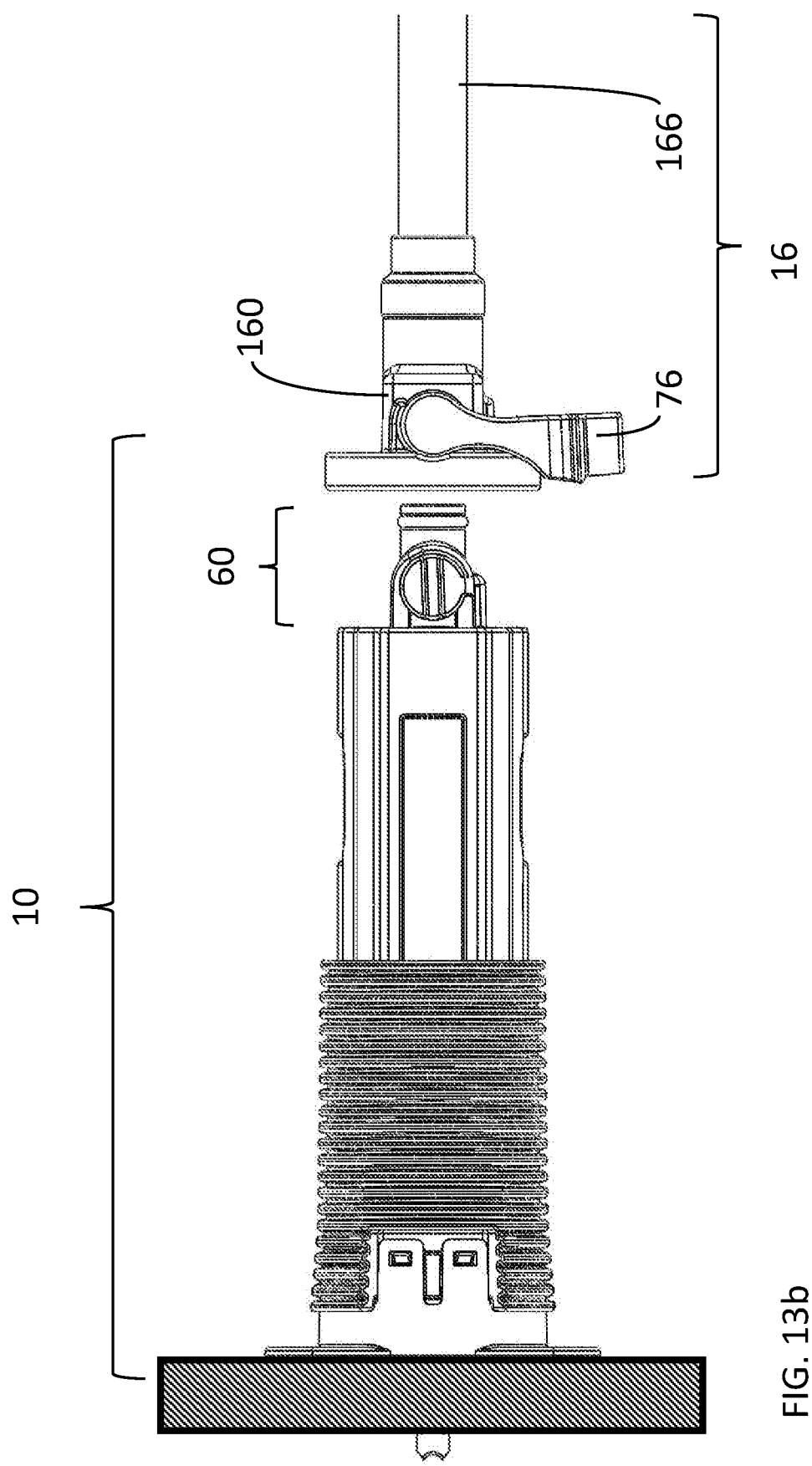
FIG. 13b is a cross-sectional side view perpendicular to that of FIG. 13a of the access pathway and an attachment device in accordance with an embodiment of the present invention, shown prior to connection of the two components.
Figure 14:
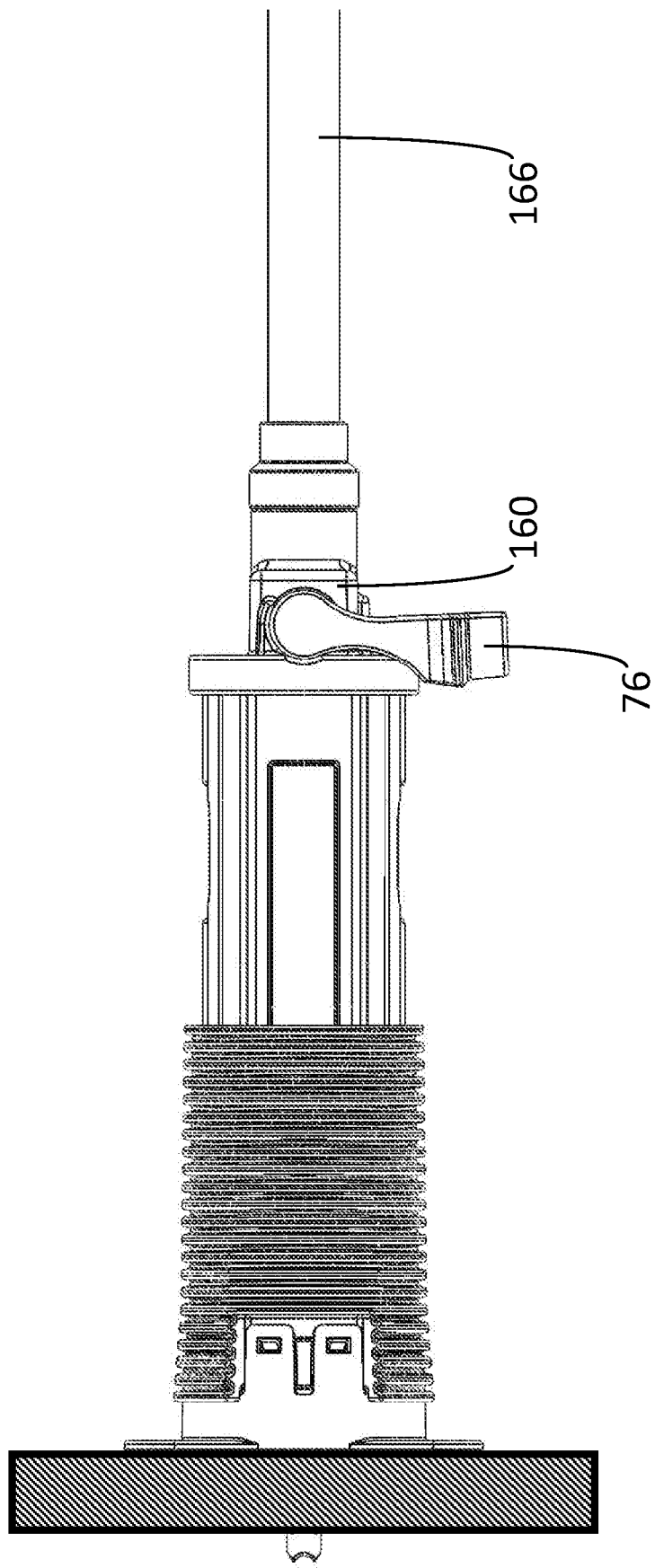
FIG. 14 is a side view of the access pathway and an attachment device in accordance with an embodiment of the present invention, shown upon initial connection.
Figure 15:
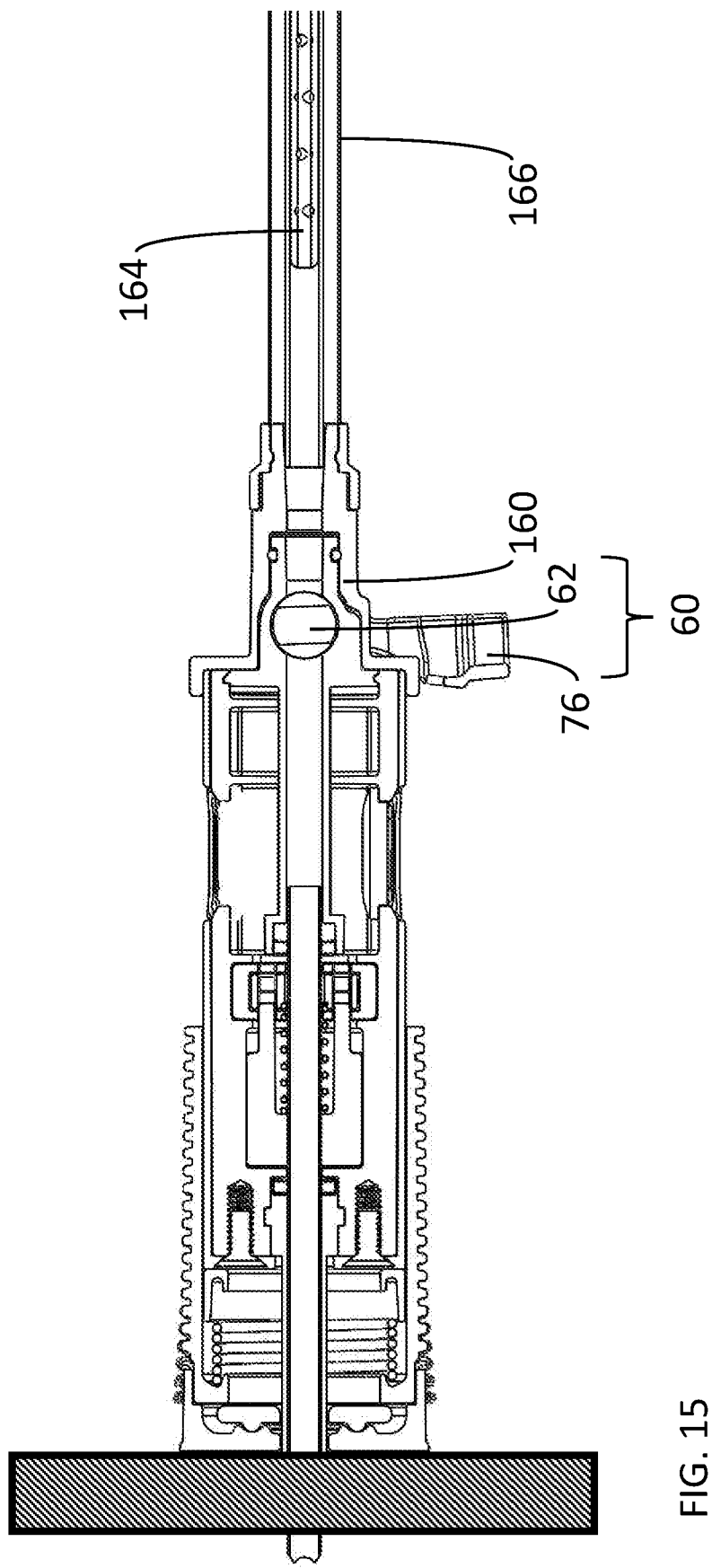
FIG. 15 is a cross-sectional side view of the access pathway and an attachment device in accordance with an embodiment of the present invention, shown upon initial connection.

FIG. 12 shows access pathway device 10 passing through skull 900 into the skull cavity after removal of drill cap 74 with lever 76 (both not shown). With drill cap 74 with lever 76 no longer present, closed port 60 cannot be easily opened by the user. This provides the benefit of maintaining the internally functionally sterile space.

FIGS. 13-16 depict the invention upon reversible connection of attachment 16 to access pathway device 10. The connection of port 60 to attachment cap 160 allows access pathway device 10 and attachment 16 to securely connect and in some embodiments form a seal, in various embodiments via direct contact, O-ring, seat, washer, and/or related mechanism. Once port 60 is opened (FIG. 16) via the movement of lever 76 by the user, there is an uninterrupted transcutaneous access pathway from the body cavity through access pathway device 10 to the inner workings of attachment 16 and whatever equipment component it has within it. For example, these figures show epidural drainage tube 164, which may be inserted into the body cavity along this path. The user can manipulate tube 164 through sheath 166 to move it forward or backwards in reference to attachment cap 160 and thus distally or proximally within the body cavity. Additionally, under some embodiments tube 164 is curved such that twisting it at its proximal end within sheath 166 or more proximally, rotationally controls direction of the distal tube end within the body cavity. Some embodiments additionally include an equipment locking mechanism, to hold tube 164 in place when not being moved by the user (not shown).

Viewing window 59 additionally allows the user to view the status of mobile stylet 20 (i.e. in its proximal or distal position). In some embodiments, this is aided by bright coloring of a portion of stylet 20 and/or components moved by it (e.g. red, green). In some embodiments, this is aided by triggering of a light, sound, or other indicating means. In some embodiments, there is no physical window, but at least a portion of the body of the device is translucent to allow viewing of this positioning. In some embodiments, an indicator of stylet 20 positioning (i.e. in its proximal or distal position) is viewed by the user from the proximal end of the device.

One benefit of many embodiments of the device is that it only allows port 60 to open when an opposing attachment cap 160 is attached and engaged. To open and engage, the user moves lever 76 on attachment 16, which moves key 163 (not shown) that is engaged with and thus turn opens port cylinder 62 on access pathway device 10. As port cylinder 62 is the inner portion of the valve mechanism of port 60, this movement makes it become in line and thus open. In many embodiments, while engaged the assembly also prevents the removal of attachment cap 160 from port 60, which provides the added benefit of ensuring that port 60 does not remain open when an attachment is not in place (i.e. not open to allow drainage and non-sterile material entrance).

Figure 16:
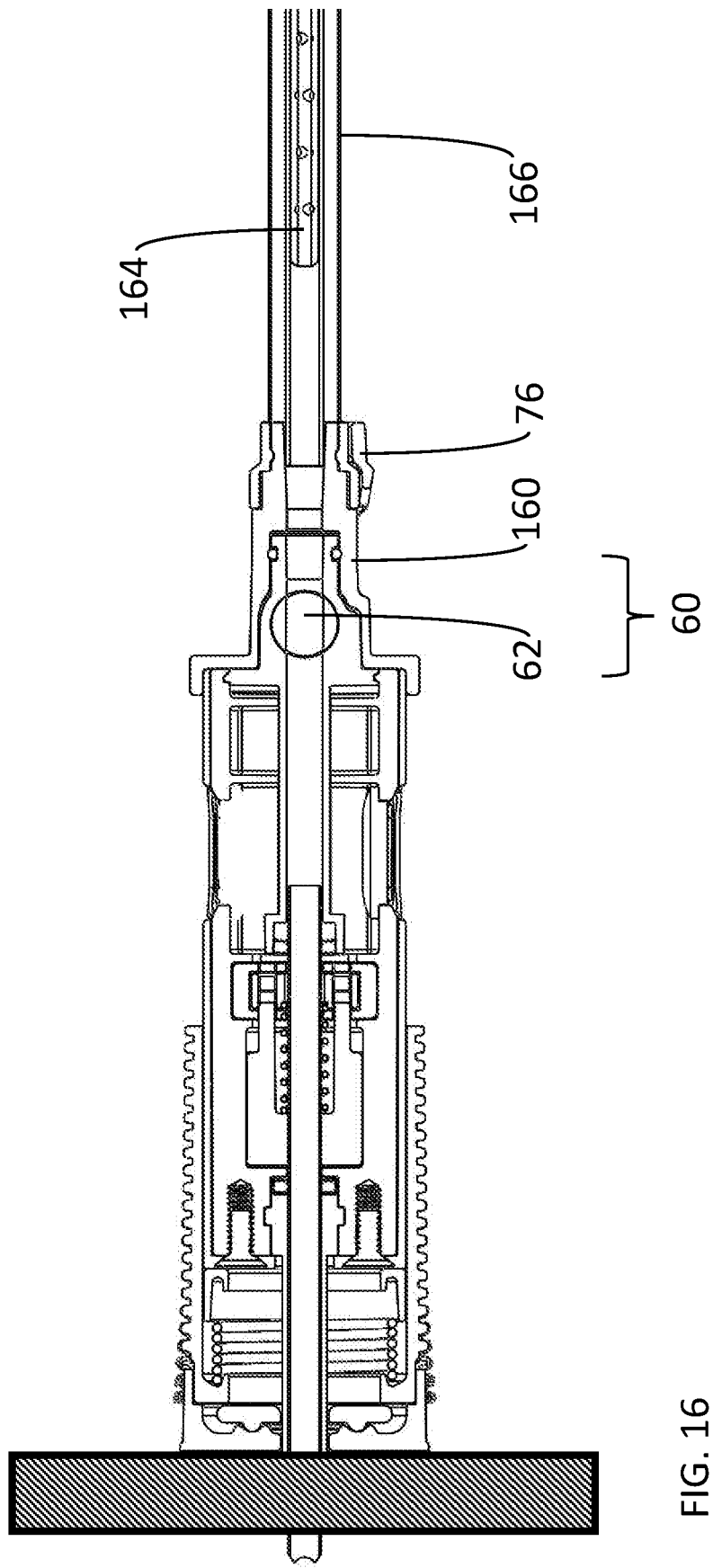
FIG. 16 is a cross-sectional side view of the device of FIG. 15, shown after opening of the port mechanism.
Figure 17:
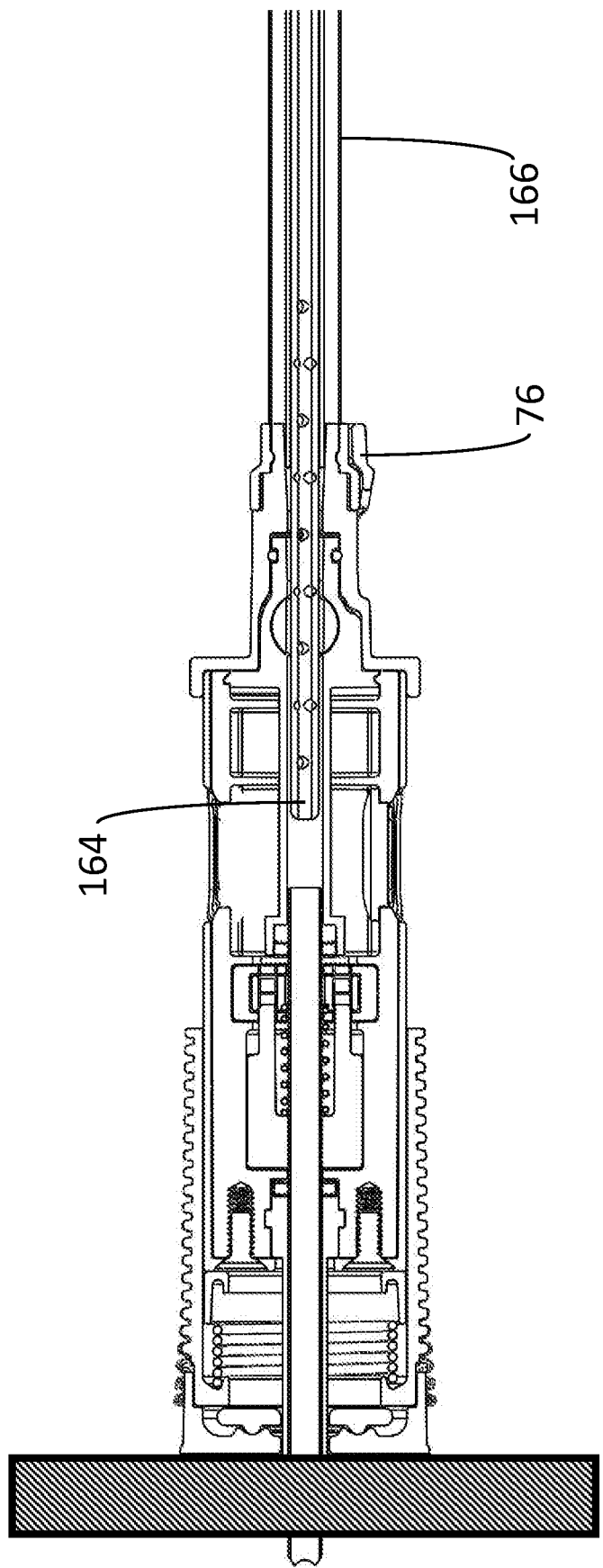
FIG. 17 is a cross-sectional side view of the device of FIG. 15, shown with the tube advancing distally.
Figure 18:
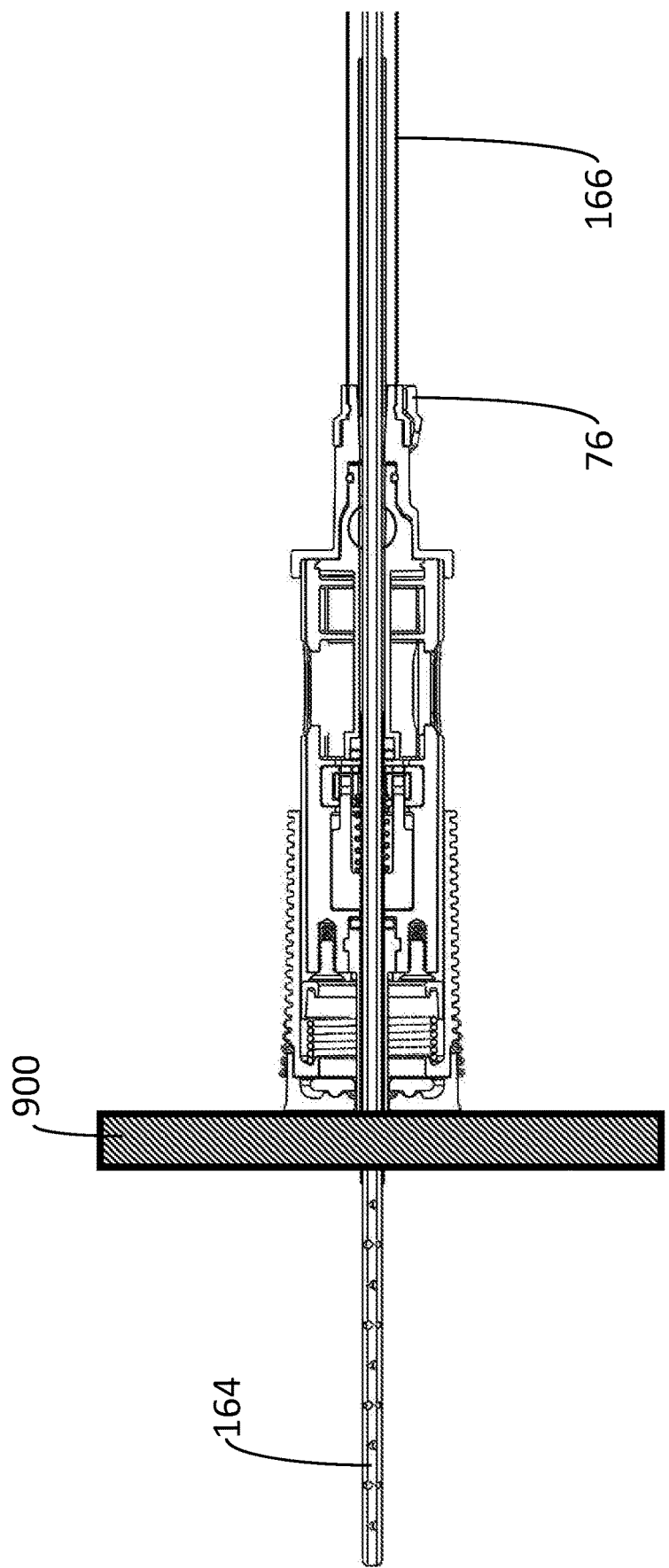
FIG. 18 is a cross-sectional side view of the device of FIG. 15, shown with the tube advanced through the access pathway and into the body cavity.
Figure 19:
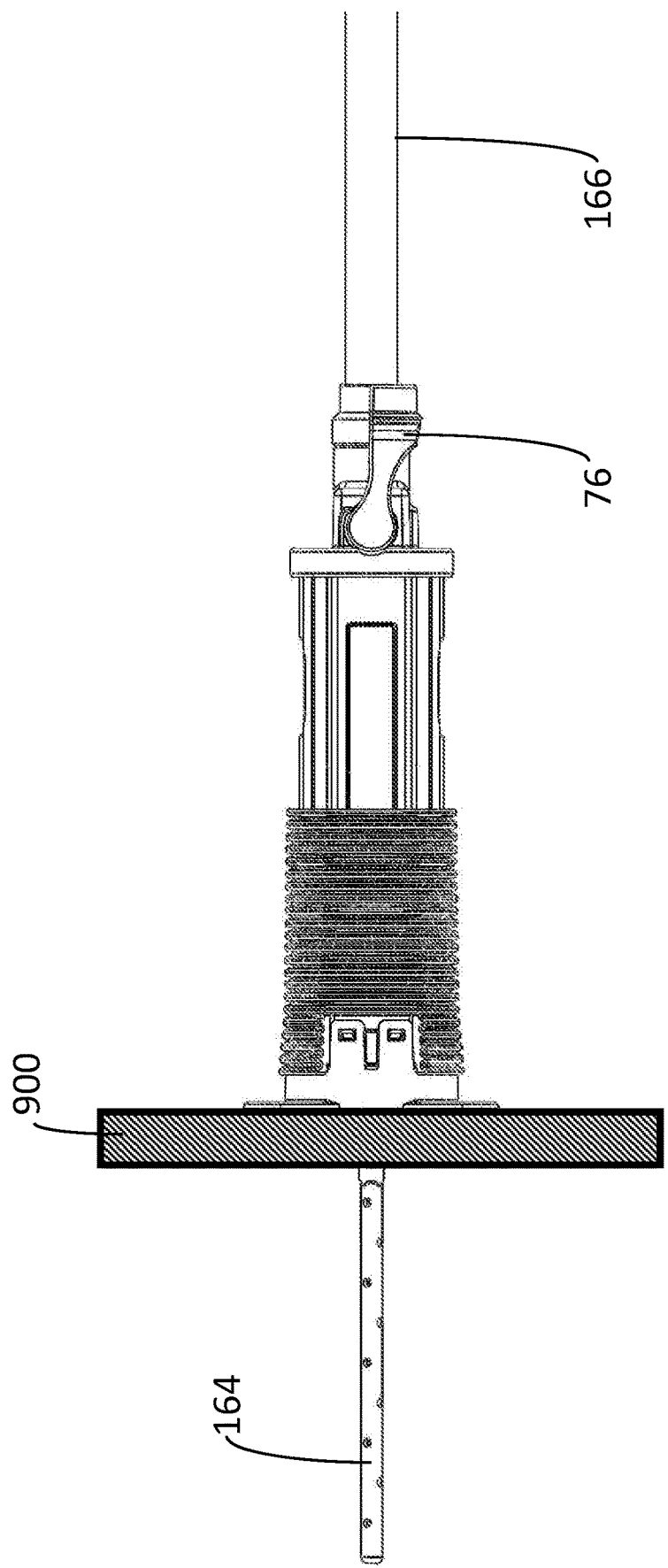
FIG. 19 is a side view of the device of FIG. 15, shown with the tube advanced through the access pathway and into the body cavity.

Referring now to FIGS. 16-18, with port cylinder 62 in its open position, tube 164 may now advance through access pathway device 10 and the patient's body cavity (e.g. cranial cavity). The opening of port cylinder 62 has created an uninterrupted transcutaneous access pathway within access pathway device 10 and attachment cap 160. As such, tube 164 can be manipulated by the operator within collapsible sheath 166 to slide it distally through access pathway device 10 and into the body (e.g. epidural space). Under many embodiments, one safety feature of the device is that attachment cap 160 is unable to be removed from access pathway device 10 until tube 164 is pulled out and port cylinder 62 closed, ensuring that the external environment does not communicate directly through an open port cylinder mechanism 62 to the body cavity (as long as the proximal end of tube 164 is sealed). In some embodiments, once tube 164 is in the desired location, an equipment locking mechanism (not shown) may be reversibly released to hold tube 164 at the desired length within the body.

Under some embodiments, when the internal equipment component of attachment 16 is a tube 164 for epidural drainage, the proximal end of the drainage tube can be connected to suction, irrigation, and/or other drainage means (e.g. Jackson-Pratt type drain) to drain from the body cavity (e.g. epidural blood). Under some embodiments, stopcock 165 is a 2-way, 3-way, or more-way stopcock. Under some embodiments, one or more syringes are additionally included in a kit to provide additional suction when connecting to the system.

Additionally, although not shown in the Figures, in some embodiments tube 164 has a check valve to prevent air and/or debris from entering the tube and body (e.g. Heimlich valve at its proximal end). Additionally, in some embodiments attachment 16 includes a device to produce vibration and/or agitation to tube 164 to better assist with suction and removal of material (e.g. retained hemothorax, pus). Additionally, in some embodiments attachment 16 includes irrigation systems to inject fluid (e.g. sterile water, normal saline, throbolytics, hemostatics, antibiotics) into the body cavity either directly through the tube or through multiple tubes and/or multi-lumen tube (e.g. irrigation through one or more lumens and suction through another). For example, under one embodiment, the internal equipment component is an irrigation-suction mechanism at least partially sealed within the sheath 164. This and related embodiments allow continuous and/or intermittent irrigation-suction to prevent and/or treat clot and/or other buildup within the body. This functions by having water, normal saline, and/or other solution enter the body through one or more irrigation lumens or tubes and then be removed by suction through one or more drainage lumens or tubes. Additionally, in some embodiments, thrombolytic agents, devices with one or more wires for tube de-clogging, and/or other prevention or treatment methods for clot are used in conjunction with the device.

Additionally, although not shown in the Figures, in some embodiments the device includes an access pathway cap that can cover port 60 when it is closed and an attachment 16 is not connected. This attachment securely covers port 60 without opening port cylinder 62, thus providing an additional barrier to entry of air, dust, dirt, and/or other external material.

Additionally, although not shown in the Figures, in some embodiments there is no port 60 (and port cylinder 62) and attachment 16 connects to intracranial access pathway device 12 through other means well known in the art (e.g. luer lock connection, quick connect). Under some such embodiments, drive assembly 14 does not have a lever 76 and attachment 16 does not have a lever 162. These embodiments may additionally include one or more caps to selectively occlude access to the access pathway, when so desired by the user.

Additionally, although not shown in the Figures, in some embodiments there is a clutch mechanism that disengages rotational energy from the drill when stylet 20 is in its distal position. Under one such embodiment, drive assembly 14 spins in connection with a drill when the drill is engaged. However, when stylet 20 is in its distal position this energy is not transmitted to the rest of intracranial access pathway device 12. When stylet 20 is moved into its proximal position (e.g. from contact with body tissue), the movement of stylet 20 causes the clutch to engage, which then causes intracranial access pathway device 12 to then rotate. When stylet 20 is moved back to its proximal position (e.g. from entering a body cavity), the movement of stylet 20 causes the clutch to then disengage, which then causes intracranial access pathway device 12 to stop rotation. This mechanism has the benefit of disengaging the rotational energy from the distal stylet and/or other device components once reaching a body cavity.

Additionally, although not shown in the Figures, in some embodiments the internal equipment component of attachment 16 is a ventriculostomy tube. This ventriculostomy tube can be utilized to perform a ventriculostomy, with its distal end in a ventricle and its proximal end connected to any one of the standard ventriculostomy monitor and/or drainage systems well known in the art.

Additionally, although not shown in the Figures, in some embodiments the internal equipment component of attachment 16 is a pressure monitor. Under some embodiments this pressure monitor is a tube that connects drainage fluid to an external pressure monitor, many of which are well known in the art. Under some embodiments the pressure is measured via an electronic sensor at the distal tip or somewhere proximal to that tip of the internal equipment component, which connects to electronic equipment to provide a pressure reading (e.g. intracranial pressure reading).

Additionally, although not shown in the Figures, in some embodiments the internal equipment component of attachment 16 is an endoscope at least partially sealed within sheath 166. In this and related embodiments, a rigid and/or flexible endoscope tube (e.g. fiber-optic scope) is partially sealed within sheath 166 with the eyepiece and/or screen for image viewing located outside of the body. These embodiments include various sizes and lenses (e.g. 0°, 30°) of endoscope. Some embodiments include an additional channel to also allow entry of medical instruments and/or manipulators. In this and related embodiments, the attachment can be used for neurosurgery other procedures involving the passage of an endoscope into the cranial cavity and/or procedures involving the passage of an endoscope into the body. Under various embodiments, these attachments facilitate the performance in a location without extensive sterility (e.g. out-of-hospital, on the battlefield, at the bedside, in the intensive care unit) of procedures currently performed in a sterile operating room (e.g. neurosurgery).

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A device for bone at least one of bone cutting and bone drilling, comprising:
    a means for providing rotational force to one or more distal rotary cutting or drilling elements that causes the one or more distal rotary cutting or drilling elements to penetrate bone;
    a clutch mechanism functionally connected to a stabilizer and configured to cause the one or more distal rotary cutting or drilling elements to penetrate bone and to automatically disengage upon bone penetration, the clutch mechanism configured to minimize the risks of the one or more distal rotary cutting or drilling elements plunging and injury to underlying structures;
    the stabilizer configured to provide counterforce from device advancement, the stabilizer configured to be disposed on a body area not immediately adjacent to the one or more distal rotary cutting or drilling elements, wherein the stabilizer allows pushback from intact skin or other soft tissues while being configured to cause minimal or no injury to the intact skin or other soft tissues, wherein the clutch mechanism includes a lock configured to selectively engage and disengage with the stabilizer, and a key configured to selectively cause the lock to engage and disengage with the stabilizer; and
    a sealable means for providing repeat percutaneous access through the device from an external environment into the body of a patient.

2. The device of claim 1, wherein the device is configured to provide access to an intracranial space.

3. The device of claim 1, wherein the clutch mechanism automatically halts forward movement of an at least partially spinning device upon penetration into a body cavity.

4. The device of claim 1, wherein a percutaneous pathway is created through the device.

5. The device of claim 1, wherein the means for providing rotational force is a housing component configured to connect to an external drill or an internal drilling mechanism.

6. The device of claim 1, wherein the device allows repeat percutaneous access through the device.

7. The device of claim 1, further comprising a means for anchoring, stabilizing, and/or securing the device to the body.

8. The device of claim 1, wherein the key is functionally connected to a stylet configured to sense penetration through bone.

* * * * *